(12) United States Patent
Baynham

(10) Patent No.: US 10,322,011 B2
(45) Date of Patent: Jun. 18, 2019

(54) SPINAL IMPLANT DEVICE WITH BONE SCREWS

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 28 days.

(21) Appl. No.: 15/874,351

(22) Filed: Jan. 18, 2018

(65) Prior Publication Data

US 2018/0153706 A1     Jun. 7, 2018

Related U.S. Application Data

(63) Continuation-in-part of application No. 15/664,891, filed on Jul. 31, 2017, now Pat. No. 10,034,767, which is a continuation-in-part of application No. 14/642,992, filed on Mar. 10, 2015, now Pat. No. 9,717,605, which is a continuation-in-part of application No. 14/294,889, filed on Jun. 3, 2014, now Pat. No. 9,445,920.

(51) Int. Cl.
    *A61F 2/44*     (2006.01)
    *A61F 2/30*     (2006.01)

(52) U.S. Cl.
    CPC .......... *A61F 2/447* (2013.01); *A61F 2/30771* (2013.01); *A61F 2/4455* (2013.01); *A61F 2/30749* (2013.01); *A61F 2002/3039* (2013.01); *A61F 2002/3093* (2013.01); *A61F 2002/30125* (2013.01); *A61F 2002/30131* (2013.01); *A61F 2002/30148* (2013.01); *A61F 2002/30153* (2013.01); *A61F 2002/30263* (2013.01); *A61F 2002/30271* (2013.01); *A61F 2002/30383* (2013.01); *A61F 2002/30405* (2013.01); *A61F 2002/30428* (2013.01); *A61F 2002/30476* (2013.01); *A61F 2002/30482* (2013.01); *A61F 2002/30507* (2013.01); *A61F 2002/30537* (2013.01); *A61F 2002/30538* (2013.01); *A61F 2002/30556* (2013.01); *A61F 2002/30578* (2013.01); *A61F 2002/30579* (2013.01); *A61F 2002/30828* (2013.01); *A61F 2002/30904* (2013.01)

(58) Field of Classification Search
    CPC .. A61F 2002/30535; A61F 2002/30576; A61F 2002/30578; A61F 2002/30579; A61F 2/44; A61F 2/447; A61F 2/4455; A61F 2/442; A61F 2/4425; A61F 2002/443; A61F 2002/4475
    USPC ................................ 606/246, 258, 249, 248; 623/17.11–17.16
    See application file for complete search history.

(56) References Cited

U.S. PATENT DOCUMENTS

| 8,398,713 B2 * | 3/2013 | Weiman ..................... A61F 2/44 623/17.11 |
| 8,556,979 B2 | 10/2013 | Glerum et al. |
| 8,709,086 B2 * | 4/2014 | Glerum .................... A61F 2/447 606/279 |

(Continued)

*Primary Examiner* — Julianna N Harvey
*Assistant Examiner* — Christina Negrellirodriguez
(74) *Attorney, Agent, or Firm* — McHale & Slavin, P.A.

(57) ABSTRACT

A spinal fusion device that is expandable. The device features a top and bottom surface for engaging adjacent vertebrae, a hollow center for stacking of bone or bone growth material, and a slidable mechanism with grooves for expanding or unexpanding compacting the device.

16 Claims, 26 Drawing Sheets

(56) References Cited

U.S. PATENT DOCUMENTS

| | | |
|---|---|---|
| 2006/0122701 A1 | 6/2006 | Kiester |
| 2009/0292361 A1 | 11/2009 | Lopez |
| 2010/0292796 A1 | 11/2010 | Greenhalgh et al. |
| 2011/0093074 A1 | 4/2011 | Glerum et al. |
| 2012/0226356 A1 | 9/2012 | Hirschl |
| 2013/0006361 A1 | 1/2013 | Glerum et al. |
| 2014/0277473 A1* | 9/2014 | Perrow .................. A61F 2/447 623/17.15 |

* cited by examiner

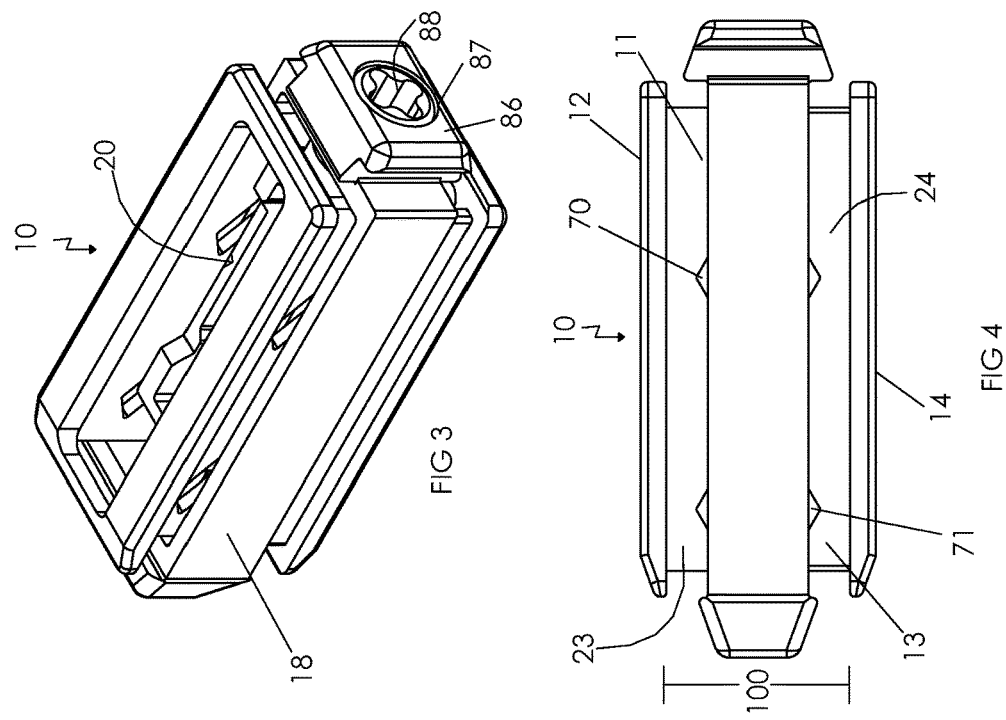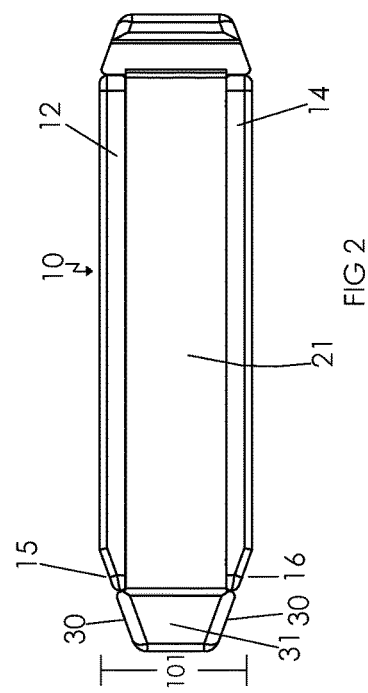

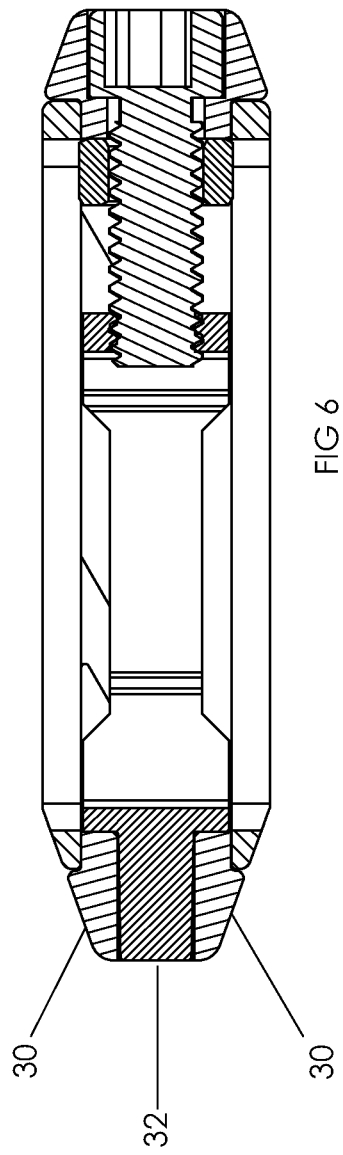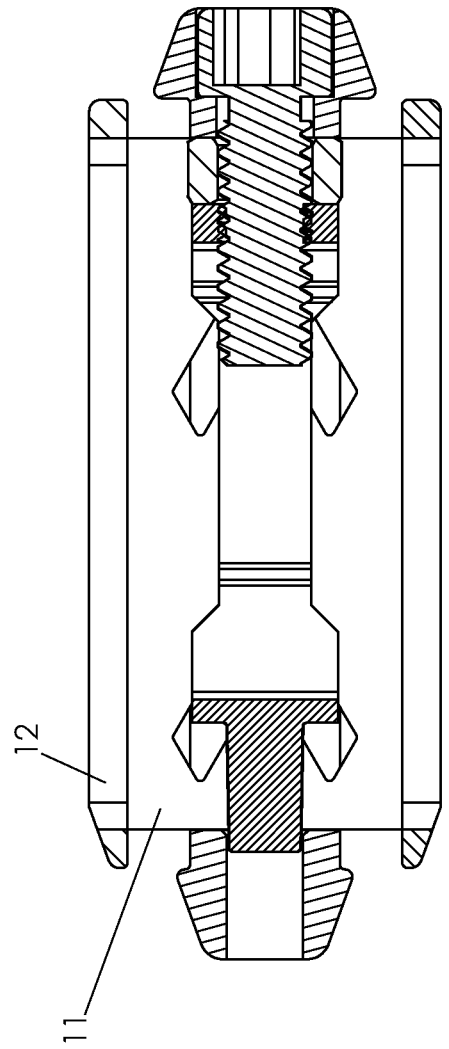

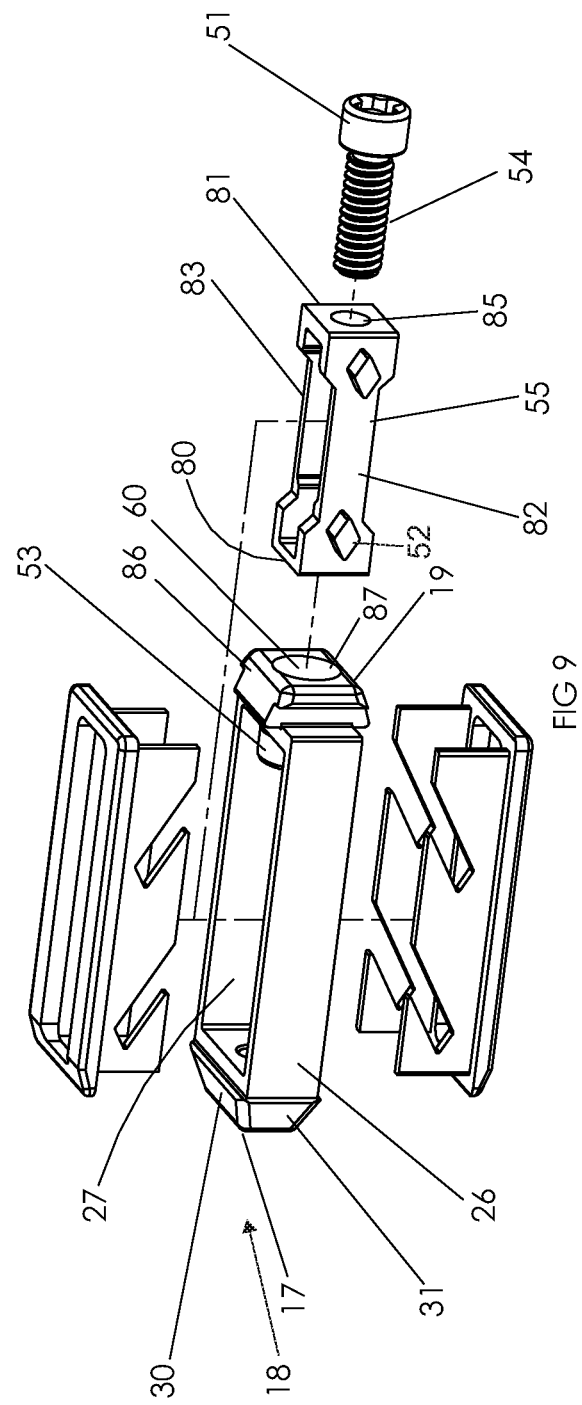

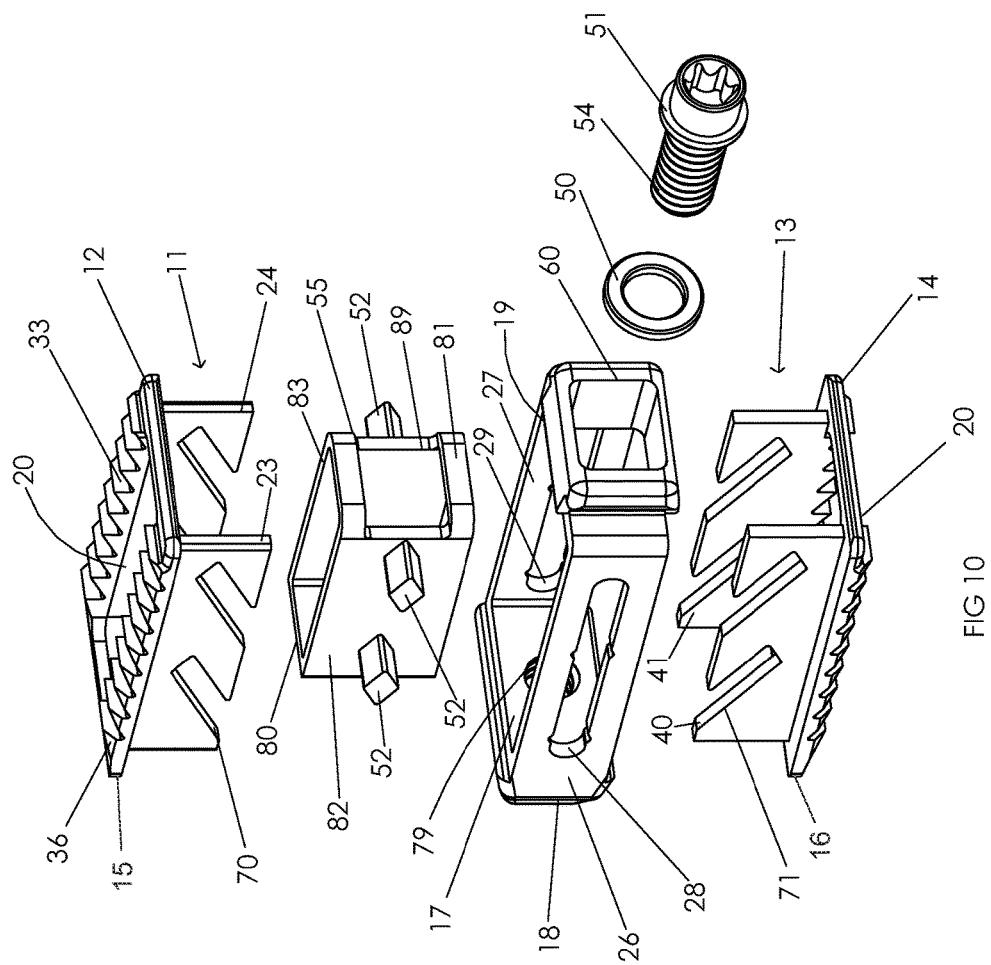

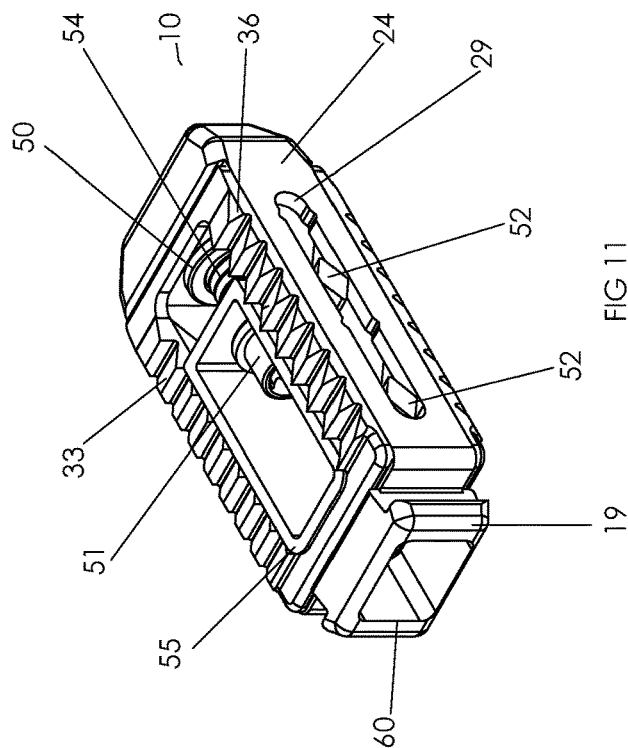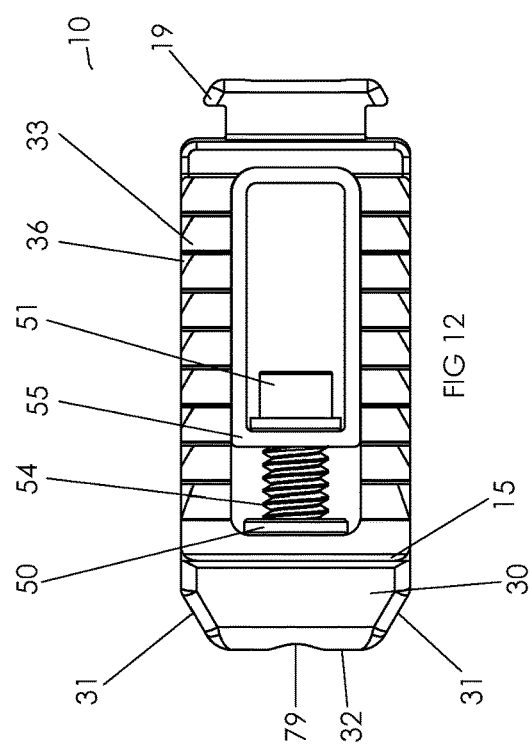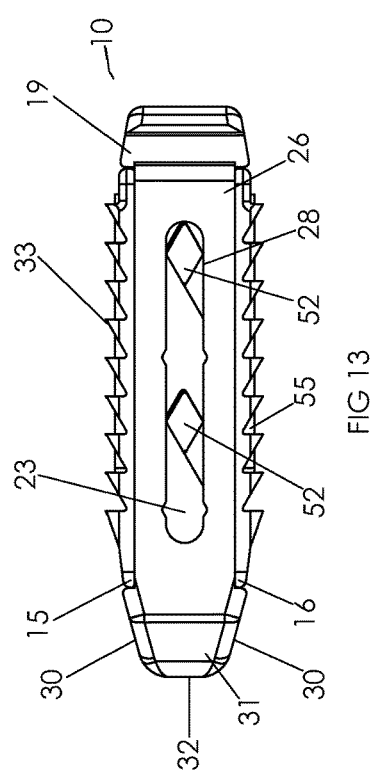

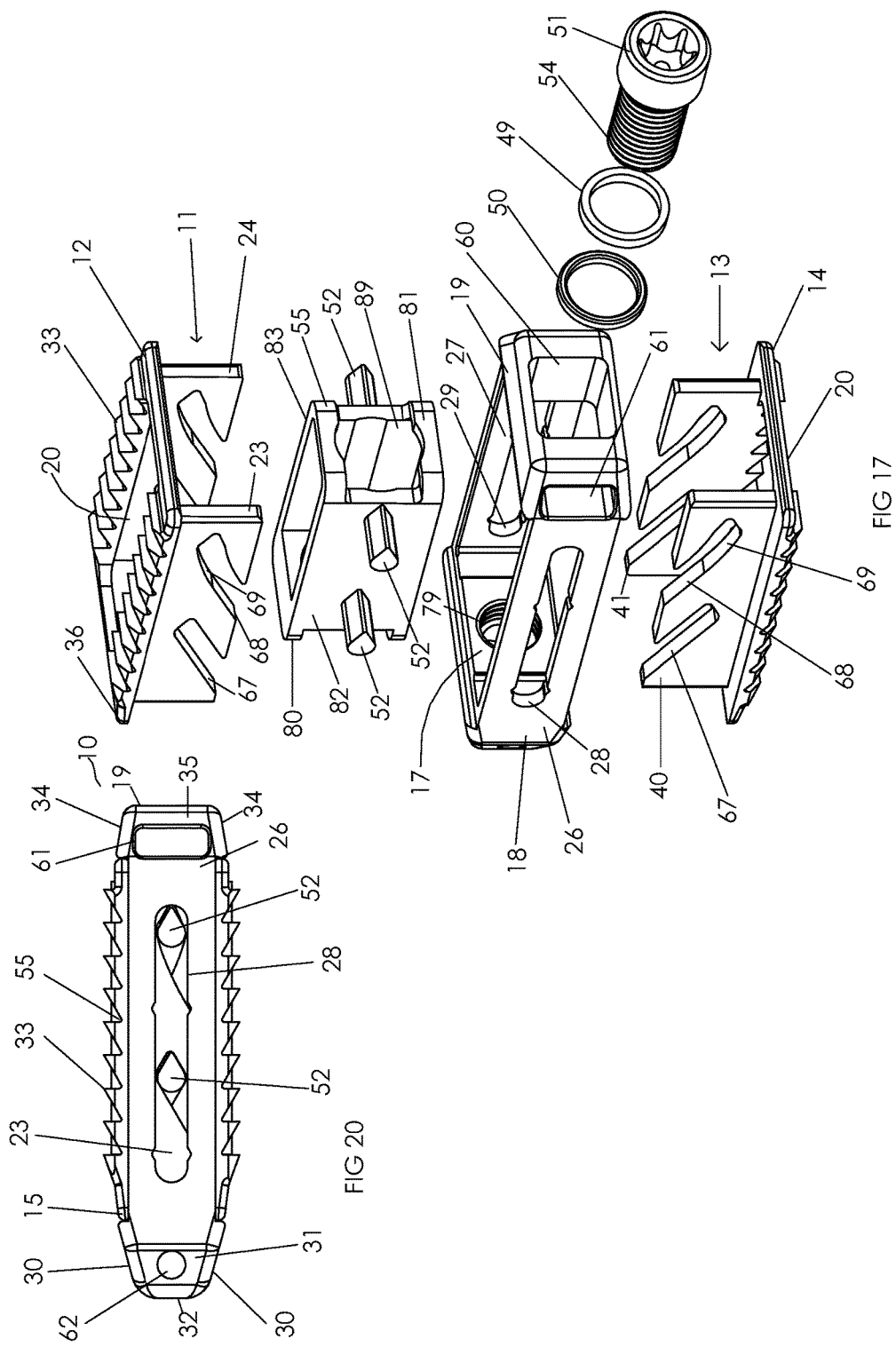

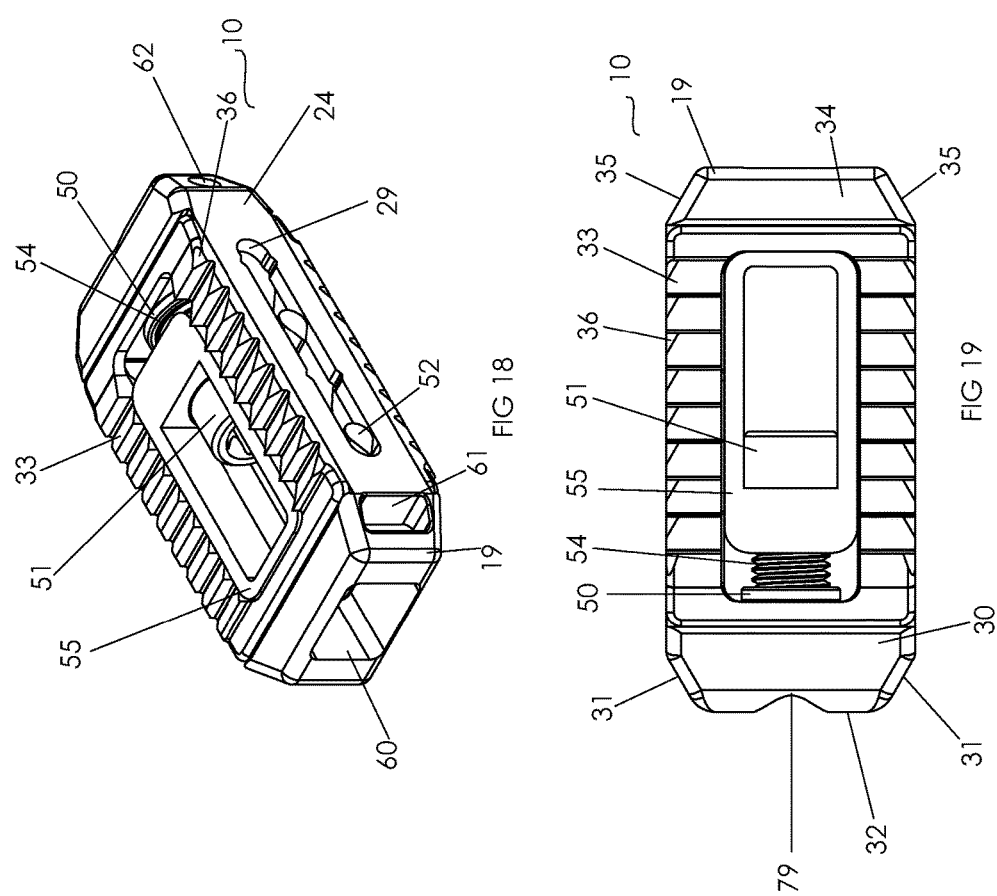

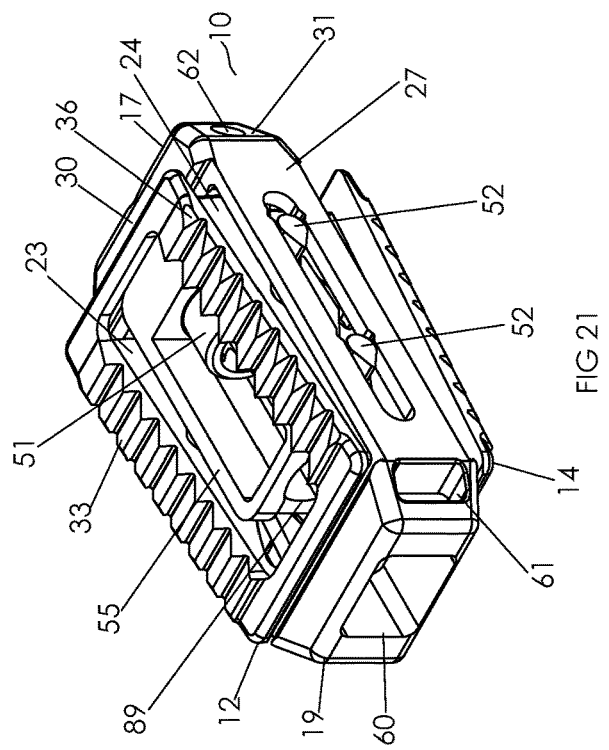
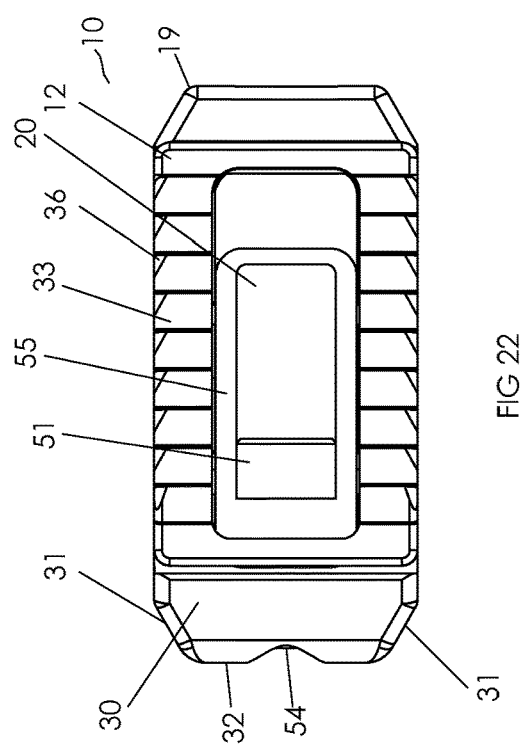
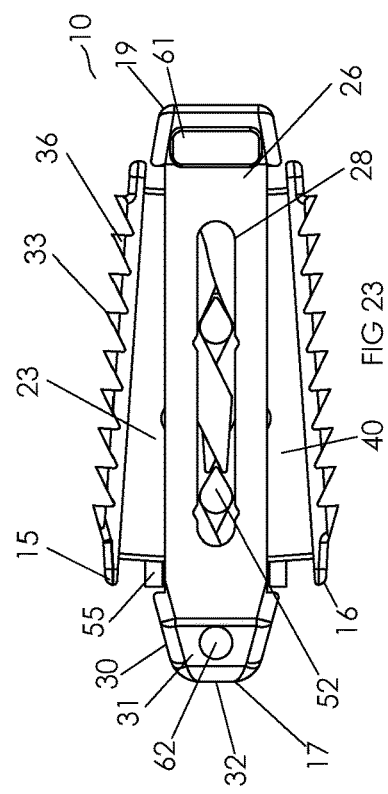

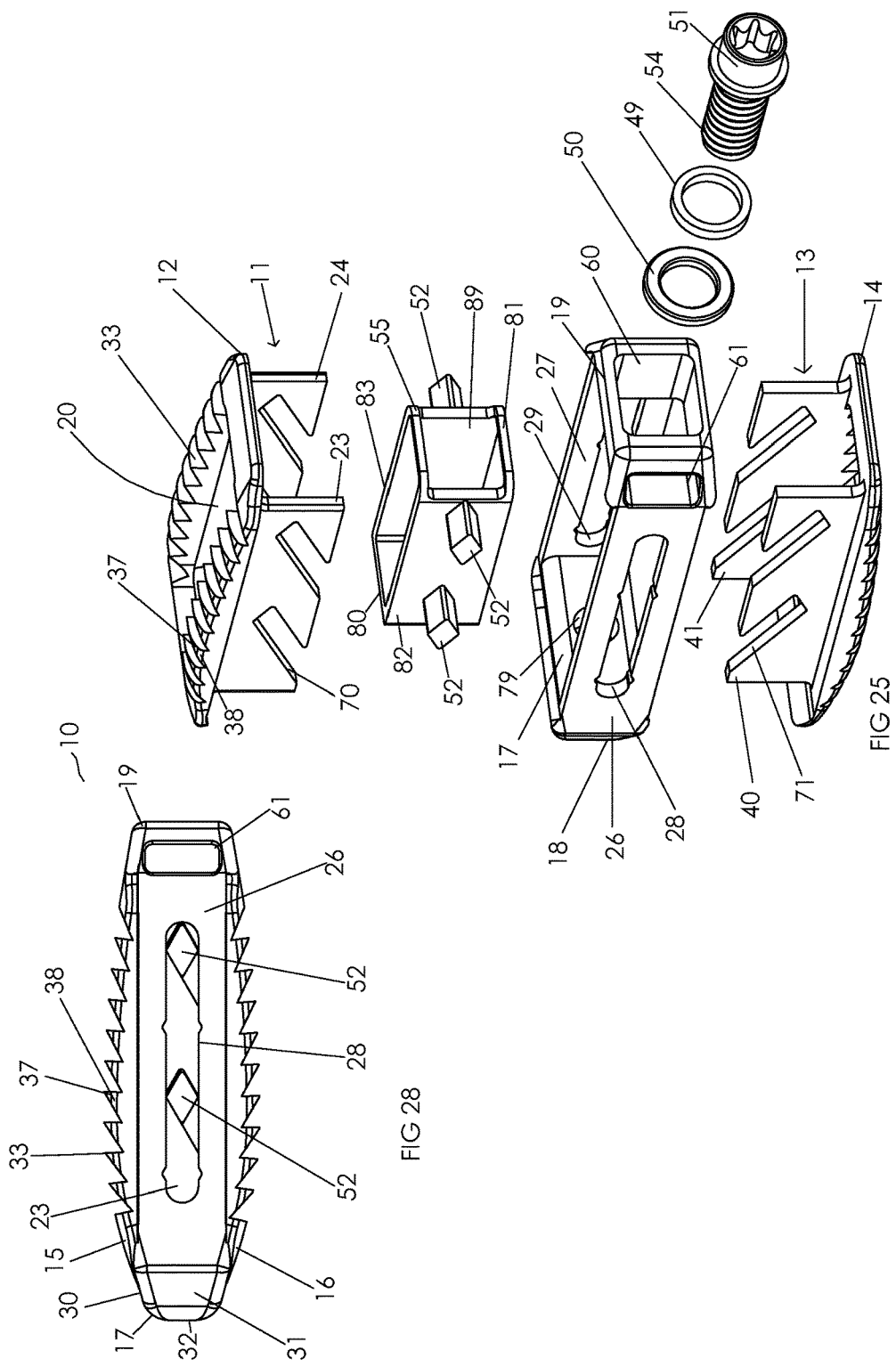

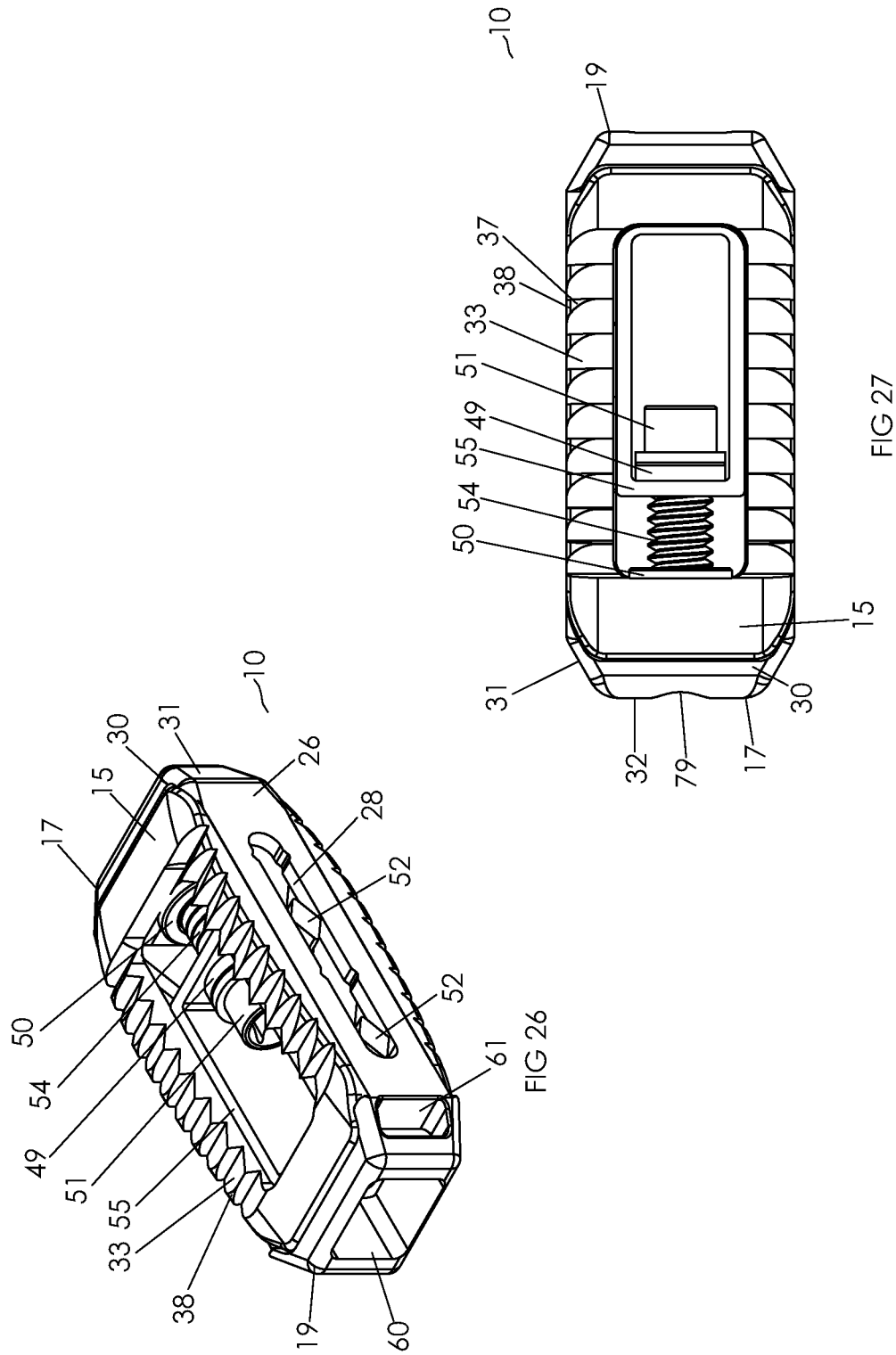

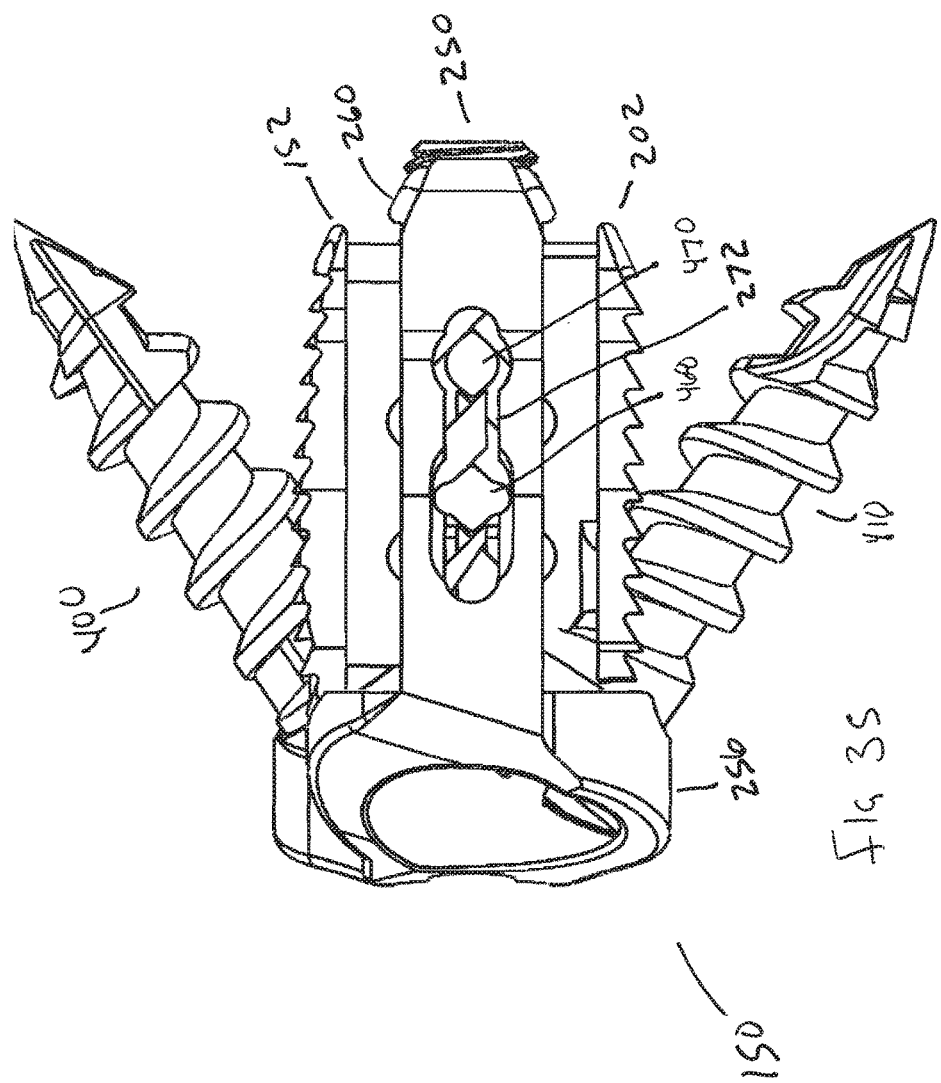

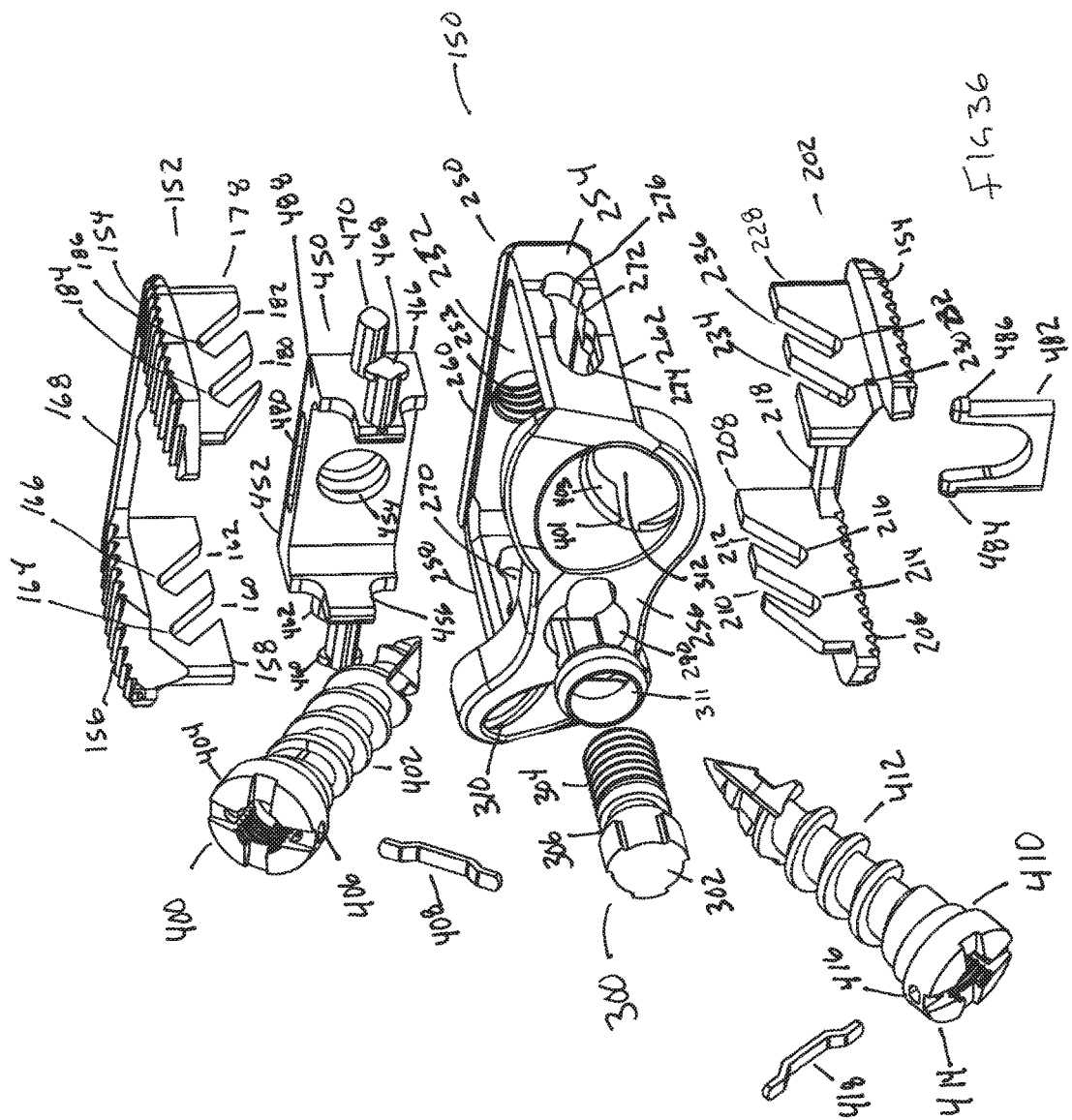

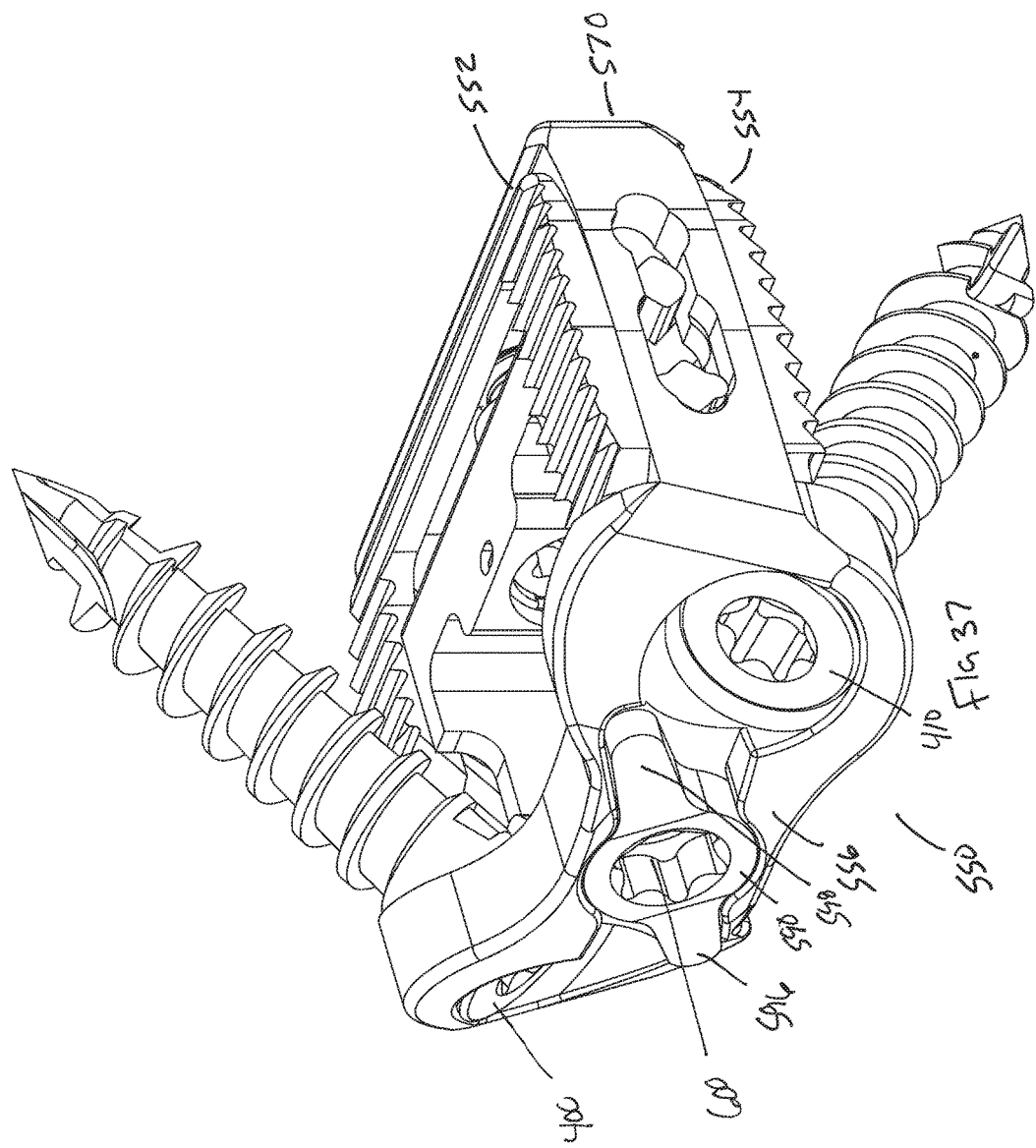

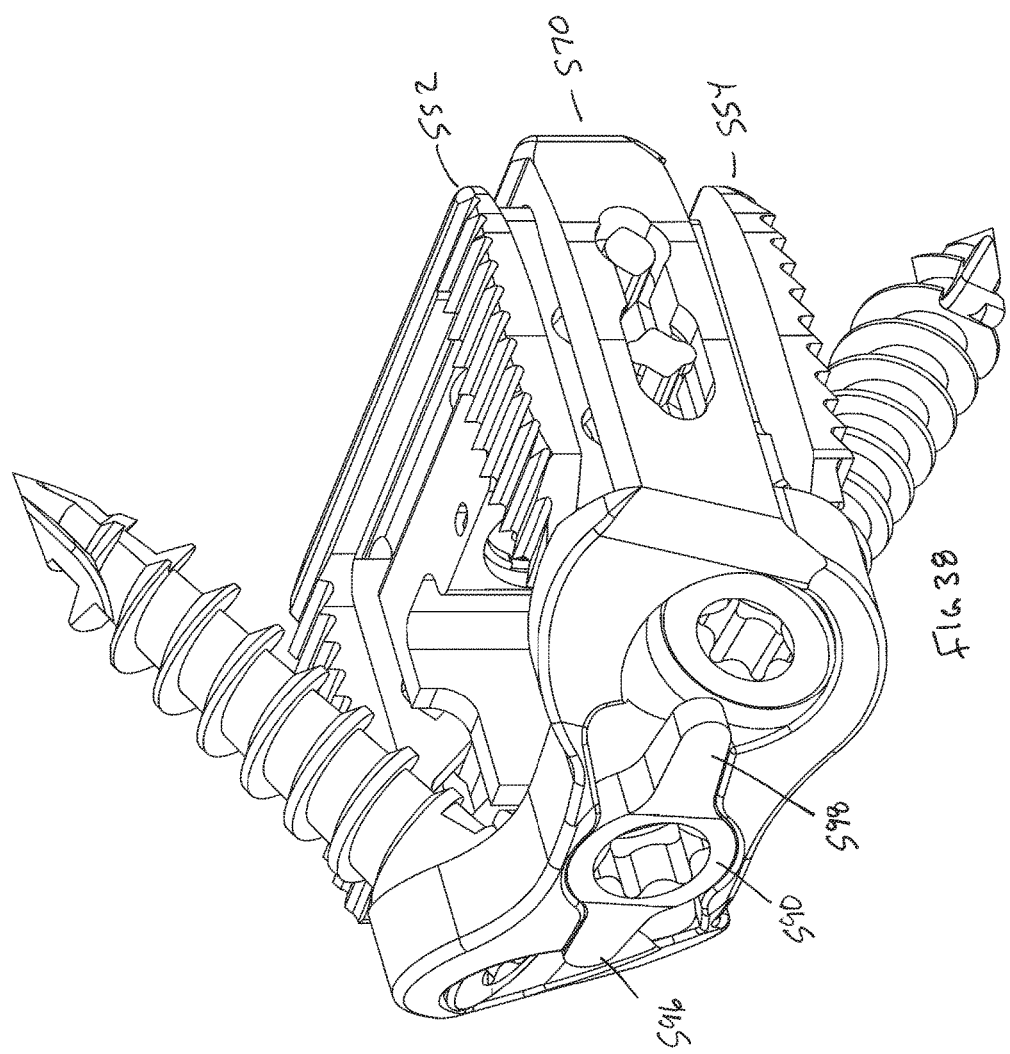

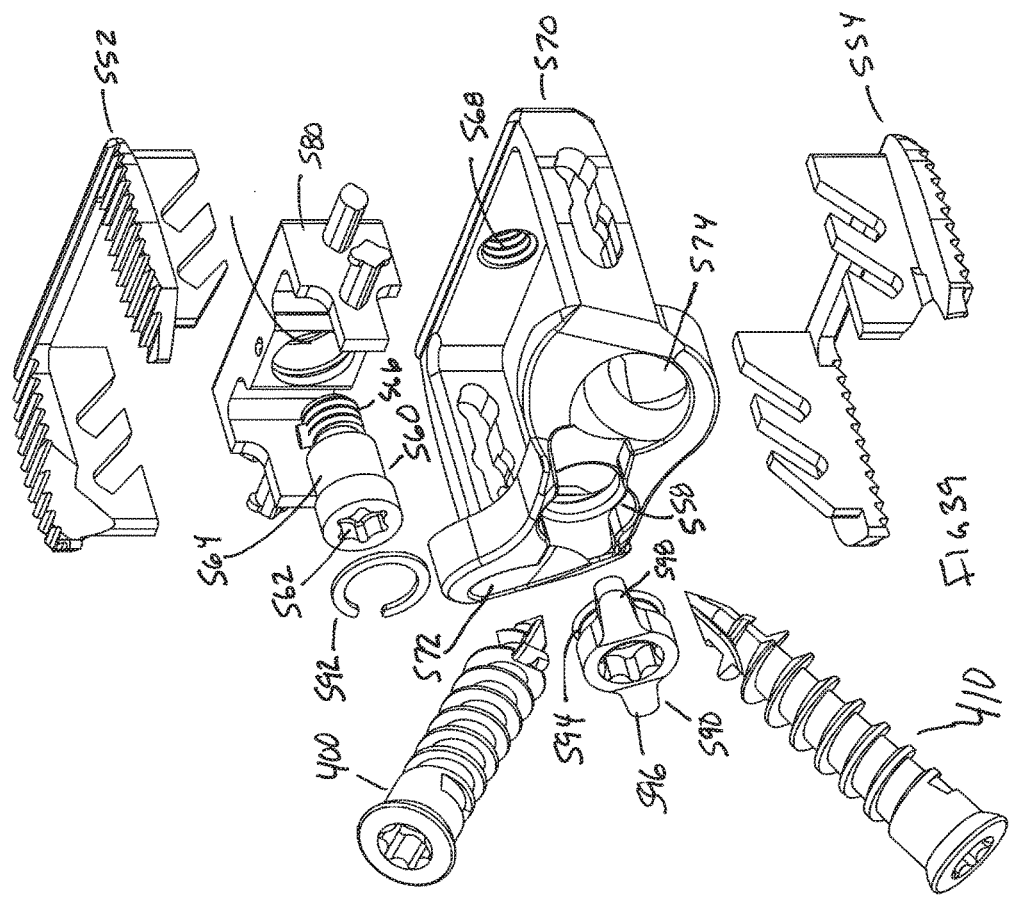

SPINAL IMPLANT DEVICE WITH BONE SCREWS

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 15/664,891, entitled "SPINAL IMPLANT DEVICE", filed Jul. 31, 2017, which is a continuation-in-part of U.S. patent application Ser. No. 14/642,992, entitled "SPINAL IMPLANT DEVICE", filed Mar. 10, 2015, now U.S. Pat. No. 9,717,605, issued on Aug. 1, 2017, which is a continuation-in-part of U.S. patent application Ser. No. 14/294,889, entitled "SPINAL IMPLANT DEVICE", filed Jun. 3, 2014, now U.S. Pat. No. 9,445,920, issued on Sep. 20, 2016. The contents of the above referenced applications are incorporated herein by reference.

FIELD OF THE INVENTION

Embodiments of the invention relate to the field of orthopedic surgery, and more particularly, to implants to be placed between vertebrae in the spine.

BACKGROUND

Spinal stabilization is one approach to alleviating chronic back pain caused by disabled disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissues. Usually the implant site is prepared to maintain natural lordosis and to accept a certain sized implant within certain pressure limits. This requires considerable time and skill by the surgeon.

DESCRIPTION OF THE PRIOR ART

U.S. Pat. No. 8,556,979, issued Oct. 15, 2013, describes an expandable fusion device capable of being installed inside an intervertebral disc space to maintain normal disc spacing and restore spinal stability. The fusion device includes a body portion, a first endplate, and a second endplate; both of these endplates can be moved in a direction away from the body portion or towards the body portion into an unexpanded configuration.

SUMMARY OF THE INVENTION

Embodiments of the invention are directed to an expandable spinal fusion device comprising upper and lower sections with depending sidewalls forming a cube-like or rectangular structure with a hollow center. The upper and lower sections comprise a top and a bottom surface, respectively, for engaging adjacent vertebrae, a slidable mechanism for expanding or compacting the device, and a hollow center allowing for packing with bone graft or similar bone growth inducing material. The slidable mechanism comprises slots or grooves on each of the sidewalls depending from the top and bottom surfaces, and a distractor. The distractor comprises a rod, a body and an actuator for enabling distraction. The rod can be telescopic or a jack screw type rod. The distractor comprises a body with protruding members, rollers or pins, for engaging the grooves which are positioned in the exact location directly opposite from each other. When the distractor is actuated, the body slides upwards, downwards or sideways depending on the groove geometry.

The device is inserted between the adjacent vertebrae and expanded or increased in height to engage the opposing surfaces of the adjacent vertebra. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion, allowing the implant to be inserted through a small incision and increased in size in situ.

It is another objective of the instant invention to teach a spinal implant which allows the surgeon to provide for lordosis intraoperatively and to distract through the implant.

It is yet another objective of the instant invention to teach an implant facilitating interbody fusion through bone graft or an ingrowth type implant.

Although embodiments are directed to posterior surgical approaches and to provide for lordosis intraoperatively, it is to be understood that the invention may be employed in cervical and thoracic spinal procedures as well as from any direction, that is, anterior, posterior and lateral.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE DRAWINGS

FIG. 2 is a side view of FIG. 1;

FIG. 3 is a perspective view of the spinal implant in an expanded position;

FIG. 4 is a side view of FIG. 3;

FIG. 6 is a cross sectional of FIG. 2;

FIG. 7 is a cross section of FIG. 4;

FIG. 9 is an exploded view of the implant without an alignment pin;

FIG. 10 is an exploded view of an alternate embodiment of the spinal implant;

FIG. 11 is perspective view of an alternate embodiment of the spinal implant device in a contracted state;

FIG. 12 is a top view of FIG. 11;

FIG. 13 is a side view of FIG. 11;

FIG. 17 is an exploded view of a wedge-expansion embodiment of the spinal implant;

FIG. 18 is a perspective view of a wedge-expansion embodiment of the spinal implant device in a contracted state;

FIG. 19 is a top view of FIG. 18;

FIG. 20 is a side view of FIG. 18;

FIG. 21 is a perspective view of a wedge-expansion embodiment of the spinal implant device in an expanded state;

FIG. 22 is a top view of FIG. 21;

FIG. 23 is a side view of FIG. 21;

FIG. 25 is an exploded view of a curved-expansion embodiment of the spinal implant device;

FIG. 26 is a perspective view of a curved-expansion embodiment of the spinal implant device in a contracted state;

FIG. 27 is a top view of FIG. 26;

FIG. 28 is a side view of FIG. 26;

FIG. 35 is a side view of FIG. 34;

FIG. 36 is an exploded view thereof;

FIG. 37 is a perspective view of an alternative screw locking embodiment of the spinal implant in an unlocked position;

FIG. 38 is a perspective view of FIG. 37 of the alternative screw locking embodiment in a locked position; and FIG. 39 is an exploded view of the alternative screw locking embodiment.

DETAILED DESCRIPTION

Figure 1:
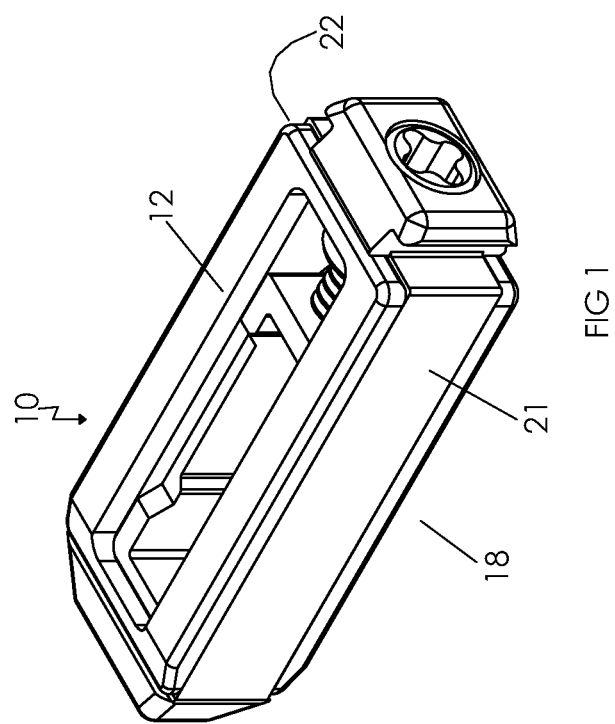
FIG. 1 is a perspective view of the spinal implant in a contracted position.
Figure 5:
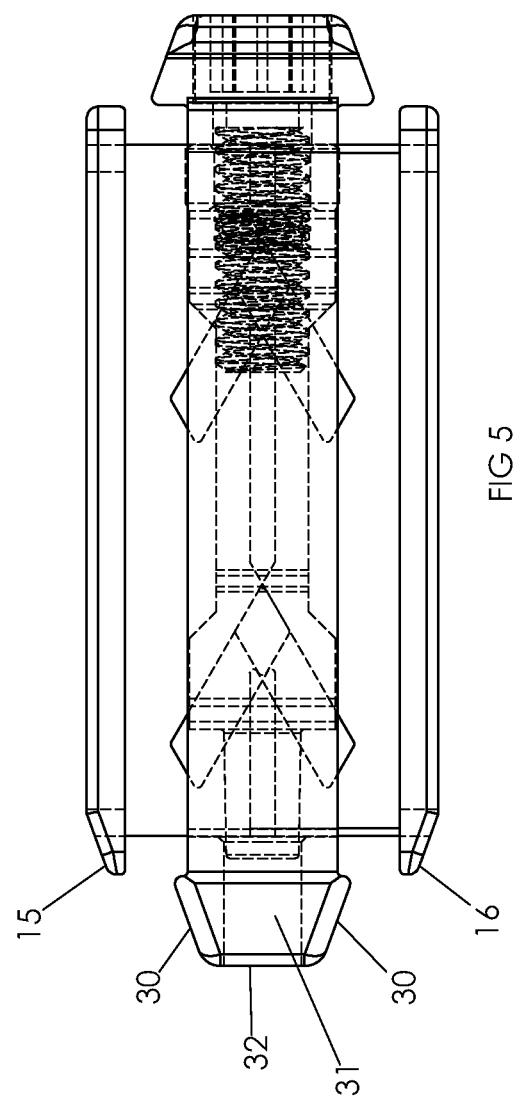
FIG. 5 is a cross sectional overlay of FIG. 4.
Figure 8:
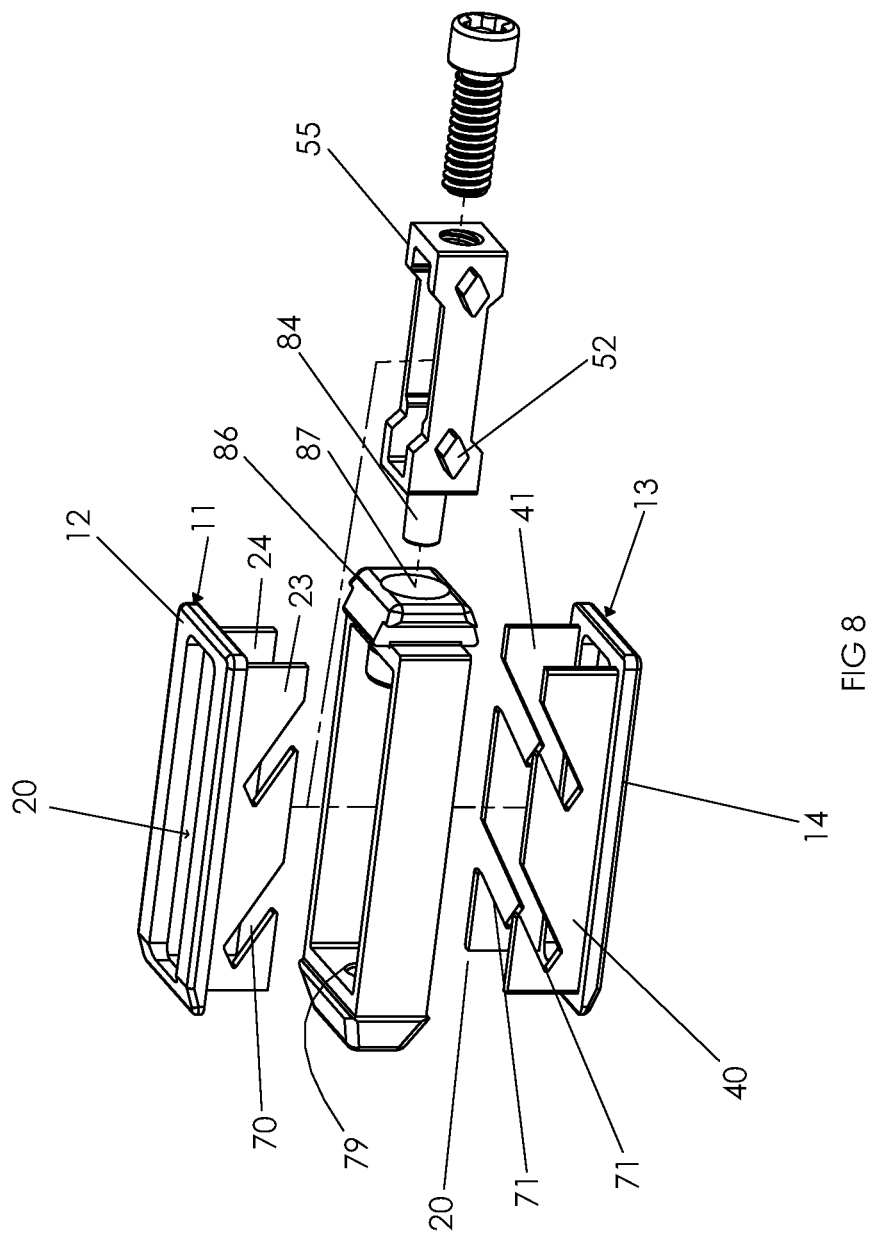
FIG. 8 is an exploded view of the implant with an alignment pin.

The following description of the preferred embodiments is merely exemplary in nature and is in no way intended to limit the invention, its application or uses.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

A spinal fusion is typically employed to eliminate pain caused by the motion of degenerated disk material. Upon successful fusion, a fusion device becomes permanently fixed within the intervertebral disc space.

Referring now to the Figures, the spinal fusion device 10 is inserted into the intervertebral space in the insertion mode to replace damaged, missing or excised disk material. In an exemplary embodiment, the device 10 comprises an upper section 11, a top surface 12, a lower section 13, a bottom surface 14, a body portion 18 and a distractor 55. The device may be made of conventional materials used for surgical implants, such as stainless steel and its many different alloys, titanium, titanium alloys, metallic alloys, polymeric materials, plastics, plastic composites, ceramic and any other metal or material with the requisite strength and biologically inert properties.

In one embodiment, the upper section 11 of the device 10 comprises a top surface 12 for engaging the end plate of a vertebra and the lower section 13 comprises a bottom surface 14 for engaging the end plate of adjacent vertebra. The top surface 12 and bottom surface 14 are planar to provide large contact areas with each vertebra. The to and bottom surfaces 12 and 14 each end at one end with a sloping or angled edge 15, 16 running the width of the top 12 and bottom 14 surfaces, respectively. The top surface ends with an edge 15 sloped towards the bottom surface, and the bottom surface comprises an edge 16 sloped towards the top surface. In other embodiments, only the top surface has a sloped edge. In another embodiment, only the bottom surface has a sloped edge. In yet other embodiments, the top and bottom surfaces lack a sloped edge.

The device 10 is hollow, allowing for insertion of bone graft, bone graft material, scaffolds or any tissue or cellular material. In one embodiment, bone graft or similar bone growth inducing material can be introduced around and within the fusion device to further promote and facilitate bone fusion. The fusion device is hollow in the center, further providing a space for packing with bone graft or similar bone growth inducing material. Such bone graft or bone growth inducing material can be packed, prior to, subsequent to, or during implantation of the fusion device.

The device 10 has two extreme positions and is adjustable infinitely between these positions. The expanded position 100 is the sum of the height of the upper section 11 and the lower section 13. The compact position 101 is the height of the sides 21 or 22 of the body portion and the sum of the thickness of the top surface 12 and bottom surface 14. The top surface 12 and the bottom surface 14 contact the body port ion 18 when the device is in a compact or unexpanded position with the upper section sidewalls 23, 24 being able to slidably fit into the hollow area. It is to be understood that the placing of the sidewalls of the upper and lower sections is interchangeable, in that the sidewalls of the lower section can be placed, at a distance further apart than the sidewalls of the upper section. In this embodiment, the upper section sidewalls slide down the inner sidewalls of the lower section sidewalls. Conversely, the upper section sidewalls can be placed at a wider distance than the lower section sidewalls so that the upper section sidewalls slide over the lower section sidewalls during the extension or when the device is in a compacted position. In another embodiment, the upper and lower section sidewalls are placed equidistant from each other so that the sidewalls rest upon each other when the device is in the unexpanded or compact position. The device can be rotated along the longitudinal axis 180 degrees so that the upper section becomes the lower section and vice versa.

The upper section 11 comprises a top surface 12 with a large aperture 20 to facilitate bon ingrowth after implantation, and opposing depending sidewalls 23 and 24 projecting from the top surface 12 and positioned parallel to each other. The depending sidewalls 23, 24 terminate in a flat plane, and each sidewall possesses at least one slot or groove 70 for engaging a protruding member, rollers or pins 52 of the distractor body 55; the protruding member 52 dimensioned to slidably fit in the slots or grooves 70. The angle of the slot or groove relative to a 90° angle to the horizontal plane of the upper section 11 can vary so that the maximum expanded position 100 can be increased or decreased. For example, with the groove close to vertical at a 90° angle to the horizontal plane, the maximum expanded position will be greater than if the slot or groove is at a 45° angle relative to the horizontal plane. However, it is to be understood that a slot or groove having, for example, a 45° angle to the horizontal plane would not only expand the upper section 11 vertically, but also displace the distractor 55 horizontally. The slot or groove 70 engages the protruding members 52 of the distractor 55 to guide the relative movement of the upper section 11, maintaining the distractor 55 and the depending sidewalls 23, 24 in alignment.

The bottom surface 14 of the lower section 13 has a large aperture 20 to facilitate bone ingrowth after implantation. The lower section 13 comprises opposing upstanding sidewalls 40, 41 projecting from the bottom surface 14 and positioned parallel to each other. The distance between the opposing sidewalls 40, 41 is dimensioned to be less than the distance between the opposing sidewalls 23 and 24 of the upper section 11 so that the upper and lower sections can slidably move between the expanded and compact positions of the device. The depending sidewalls 40 and 41 terminate in a flat plane, and each sidewall possesses at least one slot or groove 71 for engaging protruding members 52 of the distractor 55, dimensioned to slidably fit in the slots or grooves 71. The protruding member 52 can be any type, size or shape, for example, rollers, pins, as long as these protruding members 52 can be engaged by the slots or grooves 71. The angle of the slots or grooves 71 of the lower depending sidewalls 40 and 41 relative to the angle of the slots or grooves 70 of the upper depending sidewalls 23 and 24 is greater than 0° and u to 180°. The slots or grooves 70, 71 engage the protruding members, rollers or pins 52 of the distractor 55 to guide the relative movement of the upper and lower sections 11, 13, maintaining the distractor 55 and the depending sidewalls in alignment. The slots or grooves 70, 71 on each opposing sidewall are diametrically opposed on the opposite sidewalls.

The depending sidewalls of the upper and lower sections and the slot or groove of each sidewall are smooth to provide ease in the relative sliding contact between the sidewalls and between the protruding members 52 of the distractor 55. In alternative embodiments, the slots or grooves 70, 71 may comprise jagged steps which are positioned to provide a lock-step expansion when the device is expanded.

In a first embodiment, depicted in FIGS. 1-9, the device 10 comprises a body portion 18, upper and lower sections 11, 13, a distractor 55, and an actuation member 51. The body portion 18 has a first end 17, a second end. 19, a first side portion 26 connecting the first end 17 and the second end. 19, and a second side portion 27 connecting the first end 17 and the second end 19. The first end 17 of the fusion device 10 includes at least one angled surface, a grooved end and a flat end or planar end plate. The first end 17 comprises multiple angled surfaces. There are at least two opposing angled surfaces 30, 31 forming a generally wedge-shape. In other embodiments, there are at least two opposing angled surfaces 30, 31 and a flat end or planar end plate 32, wherein the angled surfaces do not meet but culminate at the flat end 32 at a first end 17, forming a generally wedge-shape; and at the opposing end, the angled surfaces culminate to form a receptacle for receiving the sloped edges of the top and bottom surfaces when the device is in a compacted or unexpanded form. In one embodiment, the top edge 15 and the bottom edge 16 are angled so as to run parallel with the angled surfaces 30 of the first end 17.

The second end 19 includes an opening 60 which may include threading. The opening 60 is dimensioned to fit a distractor 55. In one exemplary embodiment, the distractor 55 comprises an actuation member 51, a rod 54 and a distractor body 55. The actuation member 51 is located on the outer surface of the second end 19, and a member 53 of the second end 19 aligns the rod 54 with the distractor body 55. The rod 54, which extends into the hollow area of the distractor body 55, may be threaded or telescopic for slidably moving the distractor body 55 within the hollow center of the device 10. Although the term "rod" is used, it is merely descriptive and encompasses any shape or form as long as it can move the body of the distractor. In this embodiment, the distractor body 55 is dimensioned to fit in the hollow center of the device and to provide a large volume for the placing of bone graft, bone graft inducing material, scaffolds or any tissue or cellular material. In this embodiment, the rod 54 is attached to the distractor body 55. The distractor body 55 comprises a first end 80, a second end 81, a first side portion 82 connecting the first end 80 to the second end 81, and a second side portion 83 connecting the first end 80 to the second end 81. The first side portion 82 and the second side portion 83 each comprise at least one, but preferably two protruding members, rollers or pins 52 which are dimensioned to slidably fit into the grooves or slots 70, 71 in the sidewalls of the upper and lower sections. The first end 80, in exemplary embodiments, is a planar surface. In some embodiments, an alignment pin 84 is attached at the center of the planar surface of the first end 80. The alignment pin 84 may be hollow and threaded, or may be hollow and smooth, and dimensioned for insertion into support aperture 79. In some embodiments, the rod 54 is a jack screw for engagement of a threaded bore 85 at the second end. 81 of the distractor body 55. A bracket 86 is attached to the second end 19 of the body portion 18. In one embodiment, the bracket 86 comprises a bore 87 which has a larger countersunk bore 88 for receiving the rod 54. The bore 87 and countersunk bore 88 are aligned with the bore 85 of the distractor body 55. As illustrated in FIG. 9, the alignment pin can be removed and still provide stability to the distractor.

The distance between the top surface 12 and the bottom surface 14 is adjustable by moving the upper section 11 relative to the lower section 13. The protruding members 52 of the distractor 55 slide downwards when the distractor is actuated and the distance between the upper and lower section decreases. Conversely, the protruding members 52 of the distractor slide upwards when the distractor is actuated and the distance between the upper 11 and lower section 13 increases. The distractor 55 can be a telescopic mechanism, whereby the distractor comprises a member, for example, a telescopic rod, for moving the distractor body 55 by a sliding mechanism and, optionally, a locking mechanism to lock the distractor at a desired position. The distractor 55 is not limited to a sliding mechanism, but can utilize any mechanism as long as the distractor can cause the distractor body 55 to move.

The device 10 is inserted into the disk space between adjacent vertebrae with the top surface 12 in contact with the end plate of one vertebra and the bottom surface in contact with the end plate of the adjacent vertebra. When the surgeon actuates the distractor, the rod 54 is extended into the cavity, pushing the distractor body 55 and the protruding members 52 to slide along the slots or grooves 70, 71, thereby changing the distance between the top and bottom surfaces 12, 14 as the sidewalls move apart, thereby expanding the device 10. When the actuator 51 is actuated in the opposite direction, the rod member 54 retracts, pulling the distractor body 55 towards the end of the outer wall to which the distractor 55 is fastened. The extending of the rod member 54 can be accomplished by a variety of means, including a pushing or pulling mechanism or a rotating mechanism utilizing a screw and thread means. The telescopic rod, in this embodiment, comprises one or more rods of equal and/or varying lengths, each rod having a circumference slightly smaller than the previous rod so that, when the actuator is actuated, the rods can extend beyond the length of the first rod or retract into each other.

The embodiment depicted in FIGS. 10-16 includes a top surface 12 and bottom surface 14 which are constructed with friction teeth 33 for better engagement with the vertebrae. These friction teeth 33 are angled to allow the device 10 to be inserted with a lower resistance, but provide an increased resistance to the device 10 being retracted. This provides for increased stability of the device 10 between adjacent vertebrae. Additionally, the friction teeth 33 are sloped or angled on the outer edge 36, as any sharp corner edge can make insertion or proper positioning of the device 10 more difficult.

FIG. 10 is an exploded view of a preferred embodiment of the present invention. It has the same basic structure as the other embodiments of the device 10, having an upper section 11 with a top surface 12 and two opposing sidewalls 23, 24 extending inward and terminating at a plane having slots or grooves 70 to engage with the protruding members 52 of the distractor 55. The top surface 12 has an aperture 20 allowing for a channel to the hollow of the device. There is a sloping or angled leading edge 15 which abuts the first end 17 of the body portion 18 in a compact position 101.

The lower section 13 is constructed to cooperate with the upper section 11, having a bottom surface 14 and two opposing sidewalls 40, 41 extending inward and terminating at a plane having slots or grooves 71 to engage with the protruding members 52 of the distractor 55. The bottom surface 14 has an aperture 20, allowing for a channel to the hollow of the device. There is a sloping or angled leading edge 16 which abuts the first end 17 of the body portion 18 in a compact position 101.

In the preferred embodiment, the body portion 18 has apertures 28, 29 on opposing sidewalls 26, 27 which act as channels for the protruding members 52 of the distractor 55, which allow the distractor 55 to move along the longitudinal axis of the body portion 18. The opening 60 of the second end 19 of the body portion is enlarged in the preferred embodiment, allowing passage of an actuation member 51 and spacer 50 there through. The actuation member rod 54 cooperates with the support aperture 79 on the first end 17 of the body portion 18, wherein actuation moves the distractor 55 along the longitudinal axis of the body portion 18 towards the first end 17.

The distractor 55 in the preferred embodiment has a larger opening 89 on its second end 81, corresponding to the size of opening 60. Openings 60 and 89 create a passage to the hollow, whereby bone graft or similar bone growth material can be inserted into the device 10 and contact the vertebrae on the upper and lower sides of the device 10.

As depicted in FIGS. 11-13, when the device 10 is in a contracted state, the distractor 55 is back towards the second end 19. The actuation member 51 passes through an opening in the distractor first end 80, then through the spacer 50, and then enters the support aperture 79. The rod 54 of the actuation member 51 is shown here as a jack screw for engagement with the support aperture 79, which includes a bore for receiving the rod 54. The bore is aligned with the opening on the distractor first end 80.

The device is inserted into the disk space between adjacent vertebrae with the top surface 12 in contact with the end plate of one vertebra and the bottom surface 14 in contact with the end plate of the adjacent vertebra. When the surgeon actuates the distractor 55, the rod 54 is extended into the support aperture 79, pulling the distractor body 55 and the protruding members 52 to slide along the slots or grooves 70, 71 towards the body portion first end 17, thereby changing the distance between the top and bottom surfaces 12, 14 as the sidewalls move apart, thereby expanding the device 10. When the actuator 51 is actuated in the opposite direction, the rod member 54 retracts, pushing the distractor body 55 towards the second end 19, and thereby contracting the device. Actuation of the actuation member 51 causes the distractor 55 to move along the longitudinal axis of the body portion 18, guided linearly by the protruding members 52 within apertures 28, 29 of the body portion. This movement along the longitudinal axis of the body portion 18, causes the protruding members 52 to engage with the slots or grooves 70, 71. As the distractor 55 moves from the second end 19 to the first end 17 of the body portion 18, the upper section 11 and lower section 13 are forced apart, moving perpendicular to the longitudinal axis of the body portion.

The extending of the rod member 54 can be accomplished by a variety of means, including a pushing or pulling mechanism, or a rotating mechanism utilizing a screw and thread means. The telescopic rod, in this embodiment, comprises one or more rods of equal and/or varying lengths, each rod having a circumference slightly smaller than the previous rod so that, when the actuator is actuated, the rods can extend beyond the length of the first rod or retract into each other. Passage of an instrument through openings 60 and 89 allows a surgeon to actuate the actuation member 51.

Figure 14:
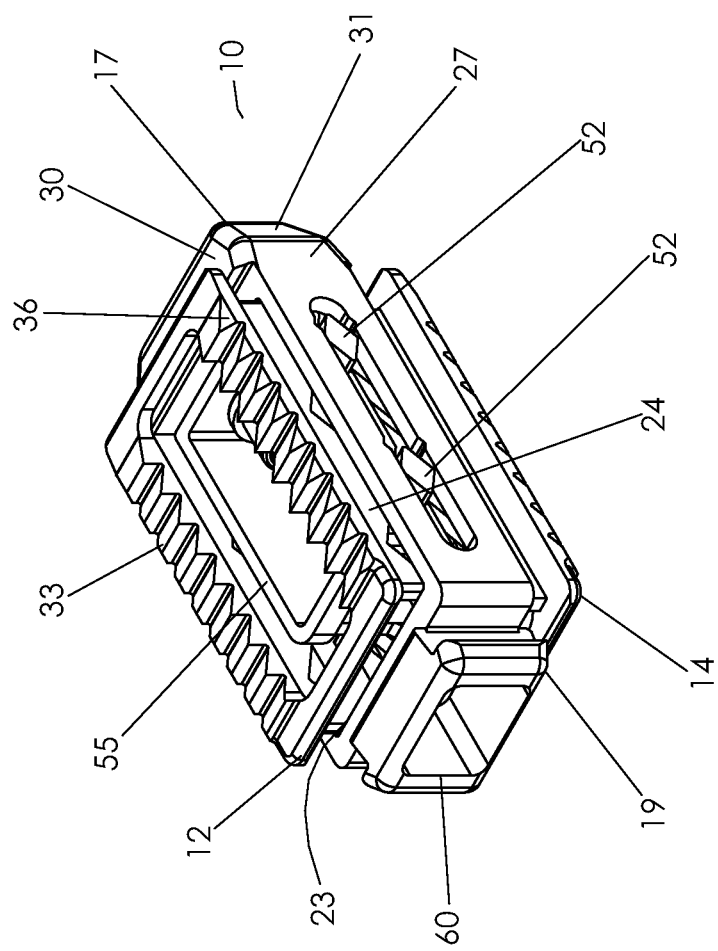
FIG. 14 is a perspective view of an alternate embodiment of the spinal implant device in an expanded state.
Figure 15:
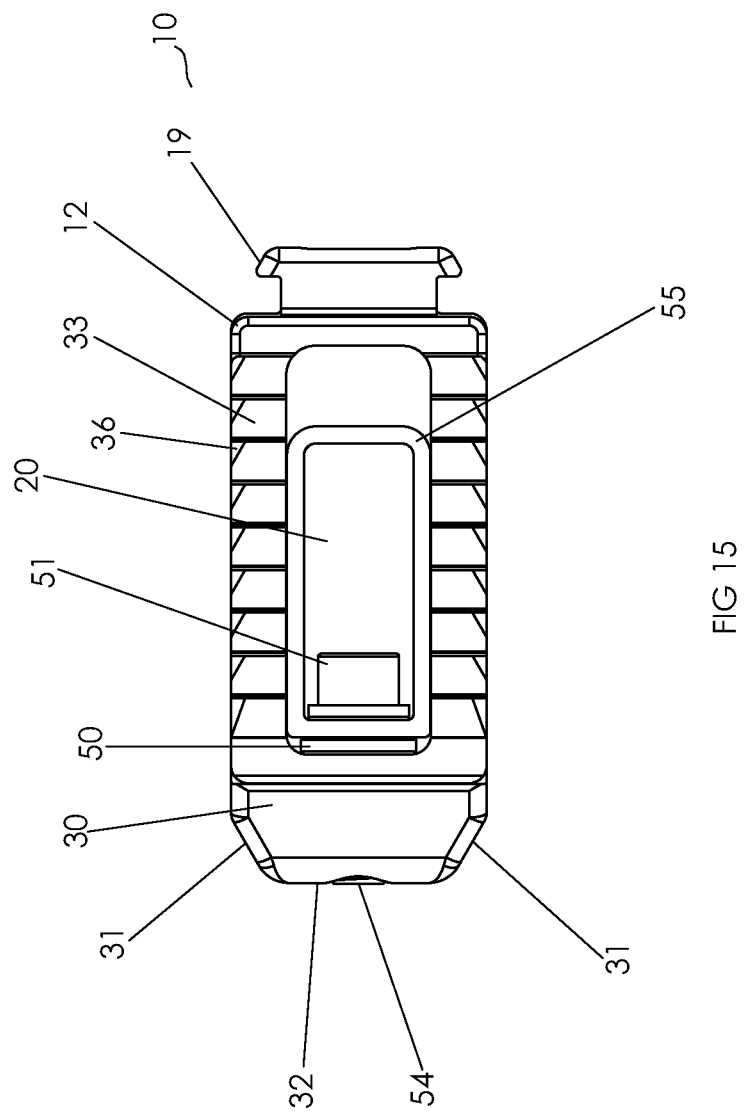
FIG. 15 is a top view of FIG. 14.
Figure 16:
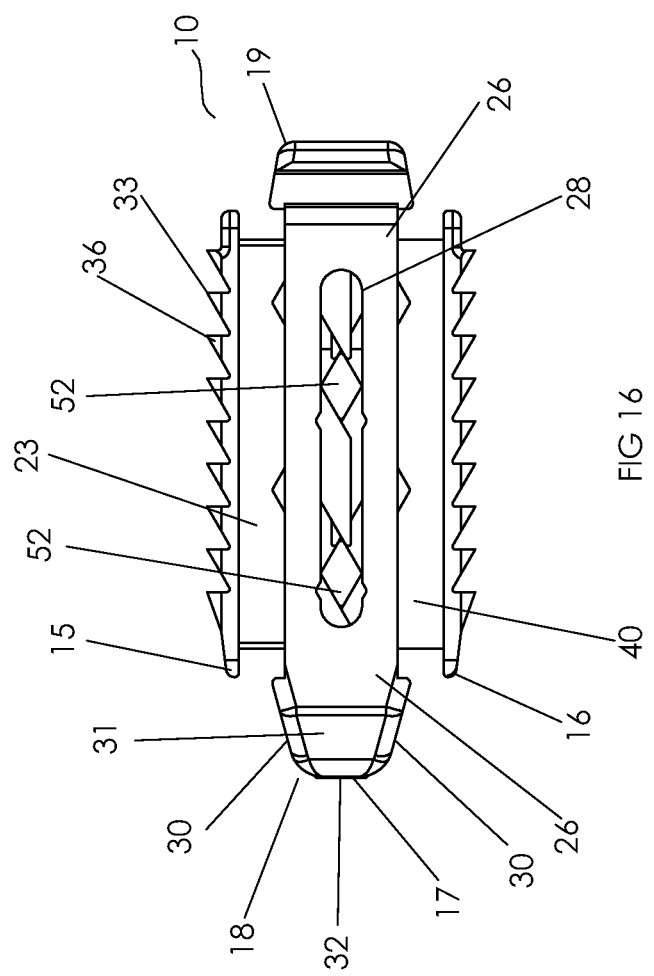
FIG. 16 is a side view of FIG. 14.
Figure 24:
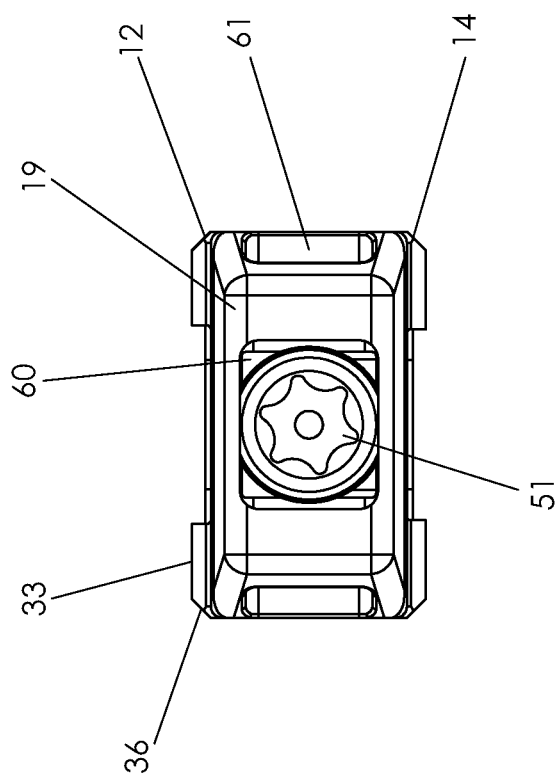
FIG. 24 is a rear view of FIG. 18.
Figure 29:
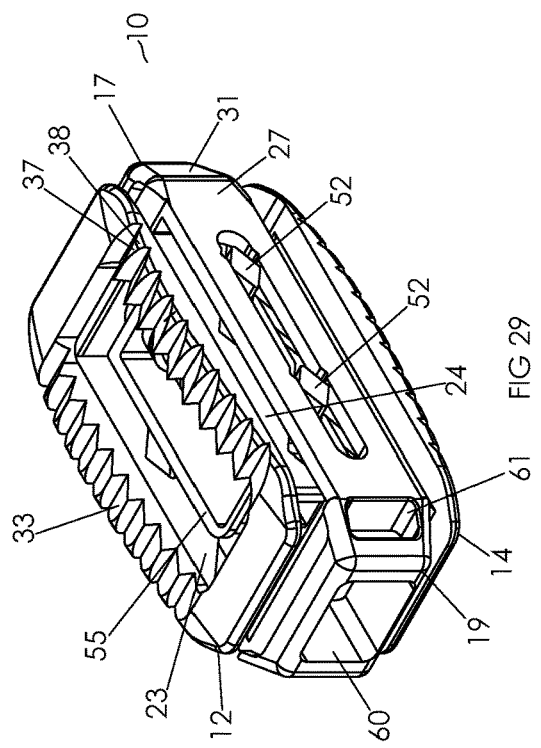
FIG. 29 is a perspective view of the curved-expansion embodiment of the spinal implant device in an expanded state.
Figure 30:
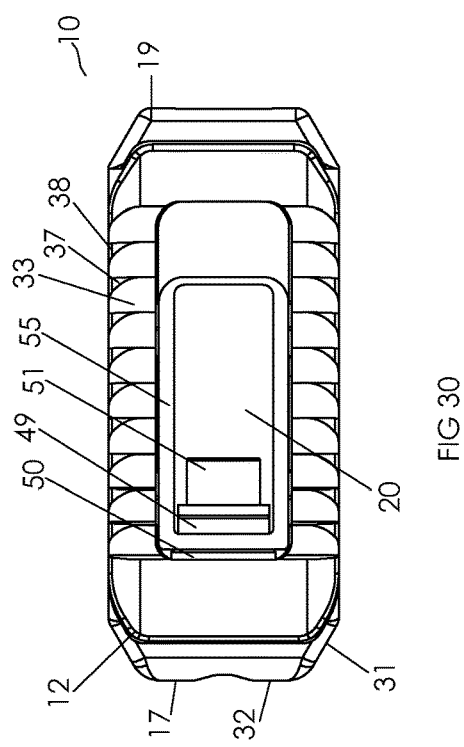
FIG. 30 is a top view of FIG. 29.
Figure 31:
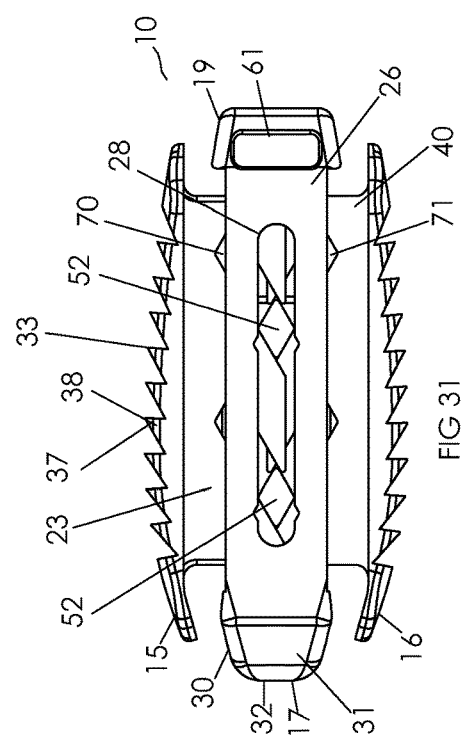
FIG. 31 is a side view of FIG. 29.

FIGS. 14-16 show the expanded state of the device 10. In an expanded state, the friction teeth 33 engage with the adjacent vertebrae to prevent movement of the device 10, now set in place.

Once the device 10 is properly positioned, the tool used for actuation can be removed, and bone graft or bone growth material can be inserted through openings 60 and 89, where it fills in the hollow of the device and flows outward to the vertebrae through openings in the top surface 12 and the bottom surface 14.

FIGS. 17-24 depict an alternate embodiment of the spinal implant device 10 which expands unevenly, forming a substantially wedge shape upon expansion. In this embodiment, the second end 19 further comprises two sets of opposing angled surfaces 34, 35, where surfaces 35 contain side opening 61 to further be able to disperse bone growth material injected into the hollow of the device 10 after insertion.

In this embodiment, a first slot or groove 67 is positioned towards the first end 17 of the device, and a second slot or groove 67 is positioned towards the second end 19 of the device. The second slot or groove 67 has a first region 68 and a second region 69, whereby the slot or groove 67 forms a shallower angle with respect to the longitudinal axis than slot or groove 66. Second region 69 is a radius, and first region 68 is a slot. Upon actuation of the actuation member 51, the distractor 55 moves along the longitudinal axis of the device 10 from the second end 19 towards the first end 17. The causes the protruding members 52 to slidably move through the slots or grooves 66, 67 until the distractor ultimately reaches the first end 17, separated by spacer 50. A second spacer 49 rests between the head of the actuation member 51 and the distractor 55.

Because of the differing angles of slot or groove 66 and 67 with respect to the longitudinal axis, slot or groove 66 causes the upper section 11 and lower section 13 to expand at a greater rate and to a greater degree than the upper section 11 and lower section 13 at the second end, which is being expanded by slot or groove 68 which has a shallower angle with respect to the longitudinal.

This uneven expansion between the upper section 11 and lower section 13 at the first end 17, as compared to the second end 13, causes the device 10 in an expanded state 100 to form a substantially wedge-shape, as depicted in FIGS. 21-23. This uneven spacing allows the device to more securely lodge into a space between vertebrae where, once the device is inserted, actuation can allow the device to expand to fill an angled gap between vertebrae, and can position vertebrae based on the amount of actuation of the actuation member 51.

FIGS. 25-31 depict a further alternate embodiment of the spinal implant device 10. In this device, the top surface 12 and the bottom surface 14 are curved about focal points within the body of the spinal implant device.

In this embodiment, the slots or grooves 70, 71 are parallel, as in the other embodiments. However, the top surface 12 and bottom surface 14 are curved about a focus in the center of the device. The expansion between the upper section 11 and lower section 13 is even because of the parallel slots or grooves, but because of the curved shape of the upper and lower surfaces 12, 14, the device has non-uniform spacing between the upper and lower sections 12, 14, between the first end 17 and the second end 19. Additionally, the friction teeth 33 have a first sloping region 37 and a second sloping region 38 adding to the curvature on the top surface 12 between the sidewall s 23, 24 and the bottom surface 14 between the sidewalls 40, 41.

This irregular spacing allows the device to more securely fit into a space between vertebrae where the bones have a similar irregular shape, such as in a cavity.

Referring now to FIGS. 32-36, illustrated is an embodiment securable to the vertebra with bone screw fasteners. In this embodiment, the spinal fusion device 150 comprises a U-shaped upper member 152 having a top surface 154 for contacting vertebra. The top surface 154 can be smooth or include teeth 156. The teeth 156 can be sloped for ease of insertion and inhibiting removal. The upper member 152 includes a first outer sidewall 158 depending from the top surface 154. The first outer sidewall 158 includes two parallel sloped slots 160, 162 formed in a first direction, wherein an upper portion 164 and 166 are positioned away from a bridge 168 that forms part of the U-shaped upper member 152. The upper member 152 includes a second outer sidewall 178 depending from the top surface 154. The second outer sidewall 178 includes two parallel sloped slots 180, 182 formed in a first direction, wherein an upper portion 184 and 186 are positioned away from the bridge 168, wherein the second outer sidewall 178 forms a mirror image of the first outer sidewall 158.

A U-shaped lower member 202 having a bottom surface 204 for contacting vertebra. The bottom surface 204 can be smooth or include teeth 206. The teeth 206 can be sloped for ease of insertion and inhibiting removal. The lower member 202 includes a first inner sidewall 208 depending from the bottom surface 204. The first inner sidewall 208 includes two parallel sloped slots 210, 212 formed in a first direction, wherein a lower portion 214 and 216 are positioned away from a bridge 218 that forms part of the U-shaped lower member 202. The lower member 202 includes a second inner sidewall 228 depending from the bottom surface 204. The second inner sidewall 228 includes two parallel sloped slots 230, 232 formed in a first direction, wherein an upper portion 234 and 236 are positioned away from the bridge 218, wherein the second inner sidewall 228 forms a mirror image of the first inner sidewall 208. The first and second inner sidewall 208, 228 are constructed and arrange to fit inboard the first and second outer sidewalls 158, 178.

The first and second outer sidewalls 158, 178 fit within a housing 250 having an inner surface 252 and an outer surface 254 formed by a front wall 256, a rear wall 260, a first side wall 258, and a second side wall 262. The first side wall 258 includes a positioning slot 270 forming a mirror image of positioning slot 272 formed in the second side wall 262. Each positioning slot 270 and 272 includes a frontal lobe 274 having an elongated flat section and a rear lobe 276 which lacks a flat section. The front wall 256 has a centrally disposed aperture 290 for receipt of an adjustment screw 300 and spacer ring 311. The adjustment screw 300 has a head 302 for ease of rotation using a driver, not shown, with the head 302 having a diameter larger than the diameter of the threaded shank 304. A lip section 306 is sized for rotation within the aperture 290 upon engagement of clip 482. The threaded shank 304 engages threaded aperture 253 formed in the rear wall 260 of the housing 250. A first offset aperture 310 for receipt of a bone screw 400 is formed along one side of the aperture 290, and a second offset aperture 312 is formed along the opposite side of the aperture 290 for receipt of a bone screw 410.

Bone screw 400 is defined by a threaded shank 402 and drive head 404. The drive head 404 includes an aperture 406 extending across the diameter of the drive head 404 for receipt of lock bar 408. Similarly, bone screw 410 is defined by a threaded shank 412 and drive head 414. The drive head 414 includes an aperture 416 extending across the diameter of the drive head 414 for receipt of lock bar 418. Each offset aperture 310, 312 includes a space 401 formed between alignment walls 403 that provide directional placement of each said bone screw. The space 401 captures the ends of each lock bar 408, 418 upon installation of the bone screw.

An actuator 450 has a body member 452 with a through-hole 454; the body member 452 having a first end wall 456 with projecting first protruding member 460 and second protruding member 462 for slidable insertion in the first side wall slot 270 of the housing 250, and a second end wall 466 with projecting first pin member 468 and second protruding member 470 for slidable insertion in said second side wall slot 272 of the housing 250. The actuator 450 includes a receptacle 480 positioned on opposing side edges of the through-hole 454 for receipt of a clip 482 for securing said adjustment screw 300 to the actuator 450. The clip 482 is generally U-shaped with tabs 484 and 486 to engage an upper surface 488 of the actuator 450 to maintain positioning of the clip 482 once installed.

Figure 32:
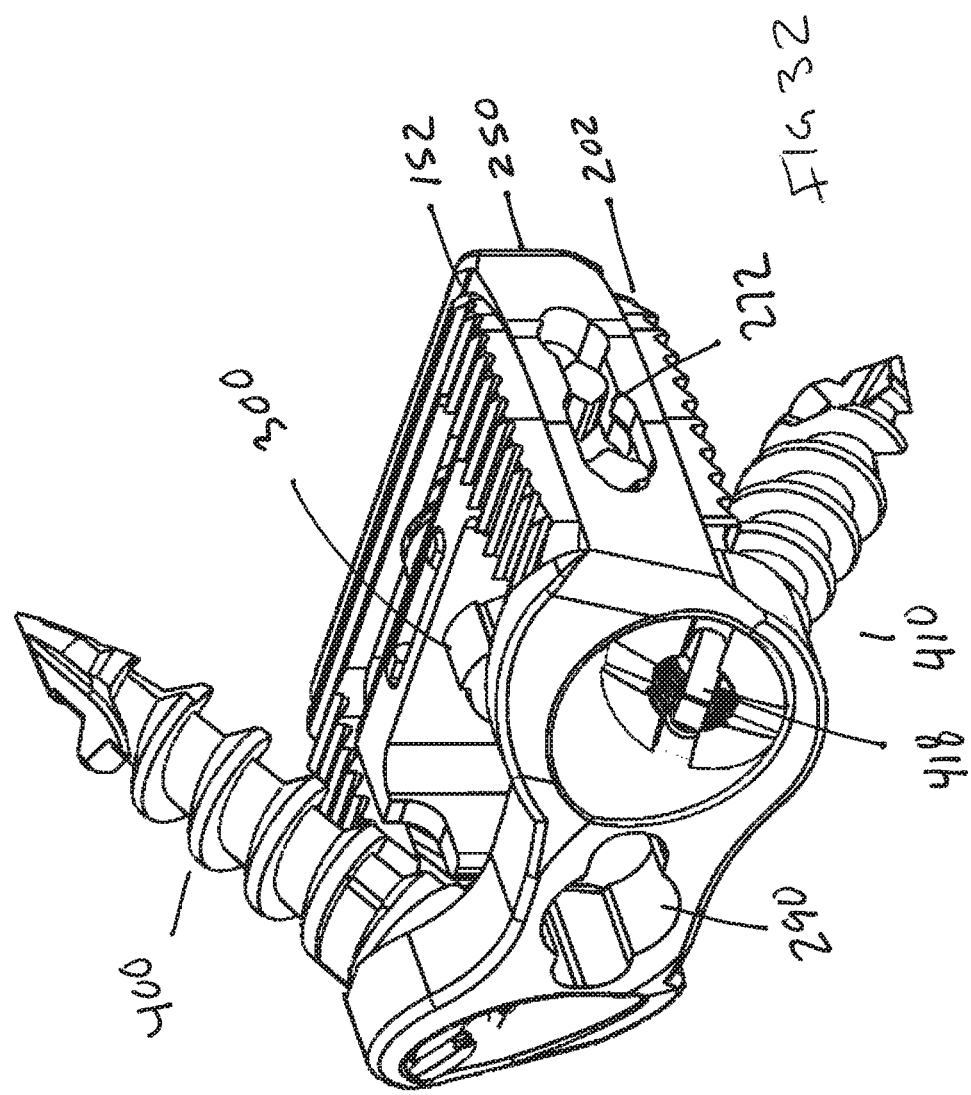
FIG. 32 is a perspective view of another embodiment of the spinal implant using pedicle screws for securement.
Figure 33:
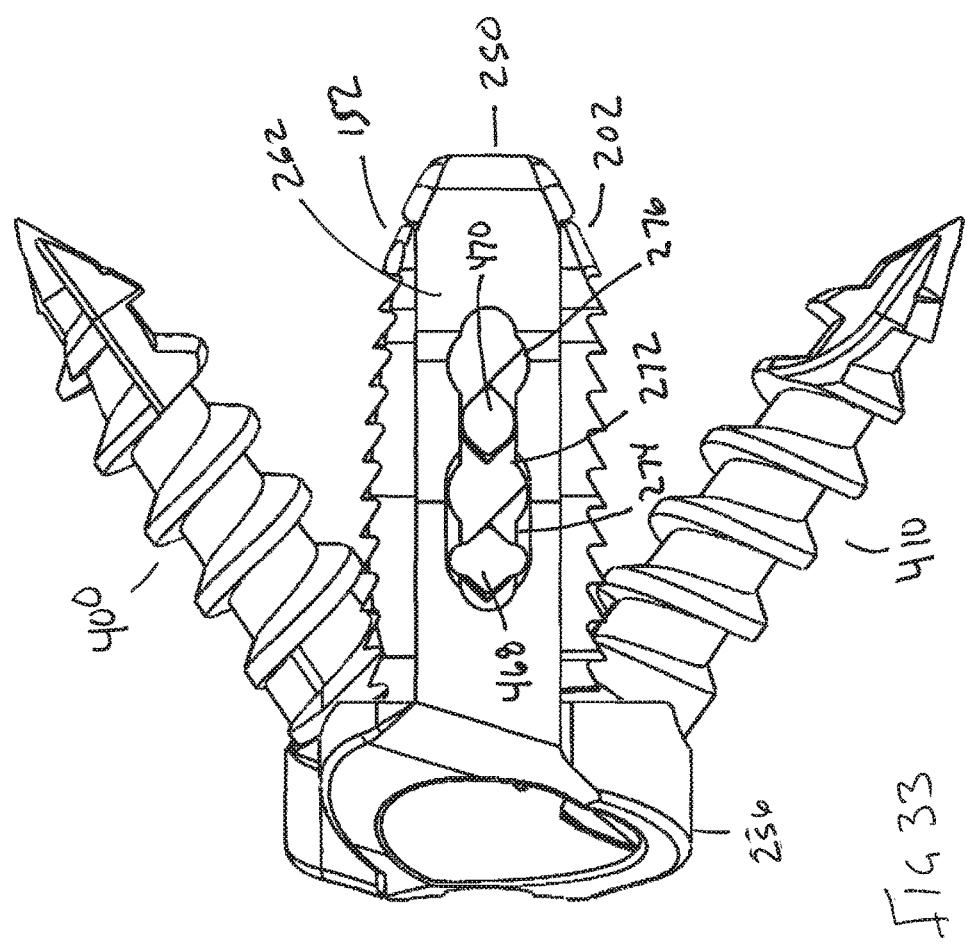
FIG. 33 is a side view thereof.
Figure 34:
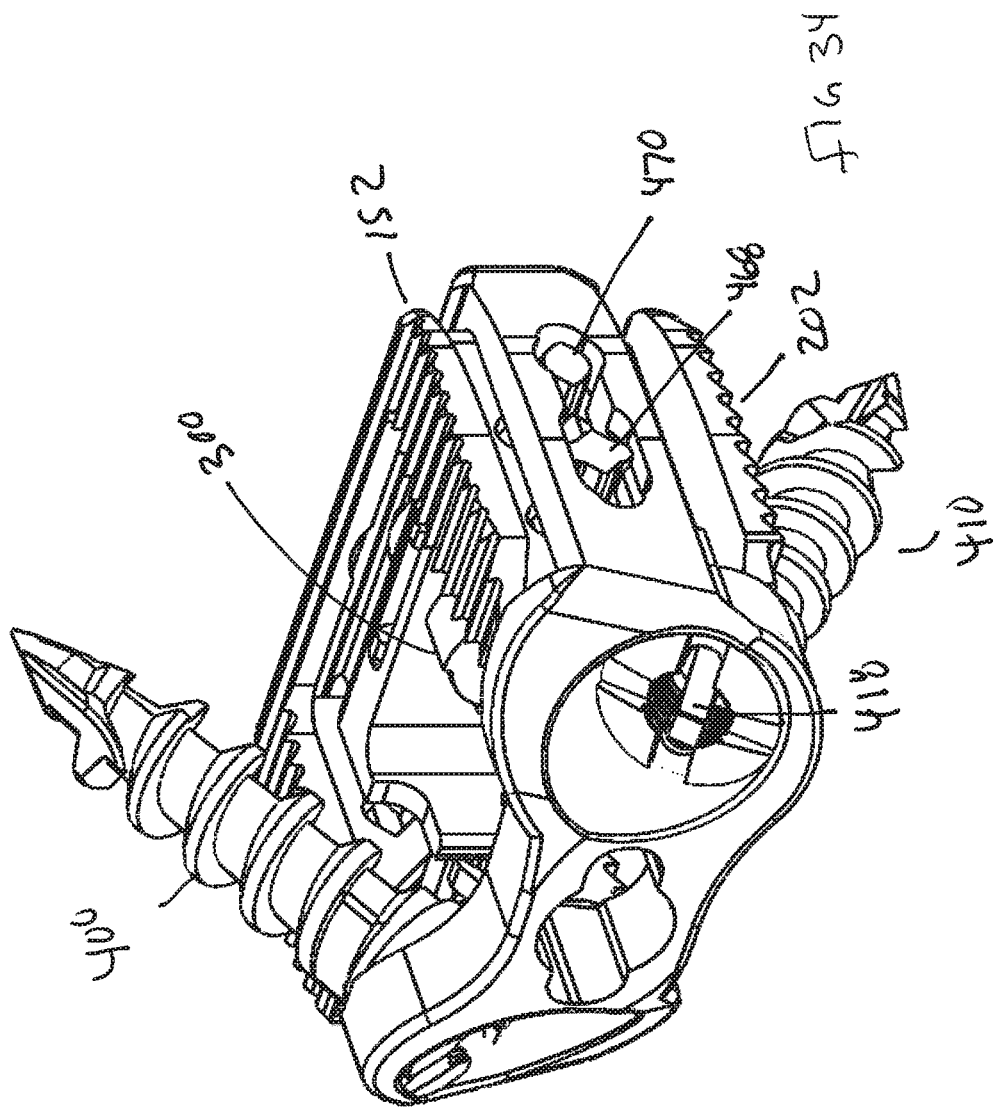
FIG. 34 is a perspective view of the spinal implant illustrating expansion.

Referring to FIGS. 32 and 33, the spinal implant device 150 is illustrated in a non-expanded position with upper member 152 and lower member 202 placed against housing 250. The positioning slot 272 formed in the second side wall 262 has a frontal lobe 274 having an elongated flat section #? and a rear lobe 276. Protruding member 468 is depicted closer to the front wall 256, and protruding member 470 is positioned near the center of the slot 272. As depicted in FIGS. 34 and 35, the spinal implant device 150 is illustrated in an expanded position with upper member 152 and lower member 202 extended apart from the housing 250. The positioning slot 272 formed in the second side wall 262 depicts the protruding member 468, which is substantially diamond shaped, moved away from the front wall 256. Protruding member 470, which is substantially oval shaped, is positioned near the rear wall 260 center of the slot 272. In operation, the device 150 is placed between adjacent vertebra with bone screws 400 and 410 inserted into the housing offset aperture 310, 312, securing the device to the vertebra. The adjustment screw 300 is rotated to move the actuator, displacing the upper member 152 and lower member 202. The actuator protruding members 460, 462, 468, 470 slidably move in the sloped slots in a first direction when the actuator is moved and the distance between the upper and lower sections decrease, and when the actuator protruding members slidably move in the sloped slots in a second direction when the actuator is moved and the distance between the upper and lower sections increase. The housing 250 is dimensioned to receive bone growth material.

Referring now to FIGS. 37-39, illustrated is an alternative embodiment having a single lock bar. In this embodiment, the spinal fusion device 550 comprises a U-shaped upper member 552 and lower member 554 having the exact same elements as the previous embodiment having upper member 152 and lower member 202. In this alternative embodiment, front wall 556 has a centrally disposed aperture 558 for receipt of an adjustment screw 560. The adjustment screw 560 has a socket 562 for ease of rotation using a driver, not shown. A lip section 564 is sized for rotation within the aperture 558 and a threaded shank 566 engages threaded aperture 568 formed in the rear wall of the housing 570. The adjustment screw 560 operates in conjunction with the actuator 580.

A first offset aperture 572 for receipt of a bone screw 400 is formed along one side of the aperture 558, and a second offset aperture 574 is formed along the opposite side of the aperture 558 for receipt of a bone screw 410. A lock bar 590 is securable to the housing 570 through the aperture 558 using a c-clip 592 to engage a lip 594 of the lock bar 590 portion that is inserted through the aperture 558. The lock bar 590 has a pair of ends 596 and 598 rotating between an unlocked position as depicted in FIG. 37 allow insertion of bone screws 400 and 410. Once the bone screws are installed, the lock bar 590 is rotated by engagement of socket 600 preventing removal of the installed bone screws 400 and 410.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

What is claimed is:

1. A spinal fusion device comprising:
    an upper member having a top surface for contacting vertebra and outer sidewalls depending therefrom having two parallel sloped slots in a first direction;
    a lower member having a bottom surface and inner sidewalls depending therefrom having two parallel sloped slots in a second opposite direction than said upper member, said inner sidewalls arranged to fit inboard said outer sidewalls;
    a housing having a front wall, a rear wall and a first side wall forming a mirror image of a second side wall, said front wall having a centrally disposed aperture for receipt of an adjustment screw and at least one offset aperture for receipt of a bone screw, said first and second side walls including a positioning slot;
    an actuator having a body member with a through-hole and a receptacle positioned around said through-hole, said body member having a first end wall with projecting first and second protruding members for slidable insertion in said first side wall slot of said housing and a second end wall with projecting first and second protruding members for slidable insertion in said second side wall slot of said housing forming a mirror image of said first slot;
    an adjustment screw engaging said through-hole;
    a clip insertable into said receptacle for securing said adjustment screw;
    wherein said device is secured by use of a bone screw inserted into said housing offset aperture, whereby said adjustment screw is rotated to move said actuator, displacing said upper and lower members.

2. The spinal fusion device according to claim 1, wherein said upper member and said lower member are U-shaped.

3. The spinal fusion device according to claim 1, wherein said offset aperture is placed along a first end of said housing and a second offset aperture is placed along a second end of said housing.

4. The spinal fusion device of claim 1, wherein said actuator protruding members engage said slots, whereby the distance between the top and bottom surfaces is adjustable as the protruding members of the actuator move within the slots, thereby moving the upper section relative to the lower section.

5. The spinal fusion device of claim 1, wherein said first actuator protruding member is substantially diamond shaped and configured to allow a side portion of said protruding member to engage one of said sloped slots.

6. The spinal fusion device of claim 1, wherein said first actuator protruding member is substantially diamond shaped and configured to allow an edge portion of said protruding member to engage one of said positioning slots.

7. The spinal fusion device of claim 1, wherein said first actuator protruding member is substantially oval shaped and configured to allow a side portion of said protruding member to engage one of said sloped slots.

8. The spinal fusion device of claim 1, wherein said first actuator protruding member is substantially oval shaped and configured to allow an edge portion of said protruding member to engage one of said positioning slots.

9. The spinal fusion device of claim 1, wherein the housing front wall aperture is constructed and arrange to allow a threaded shank of said adjustment screw to pass with a lip preventing passage of a fastener head.

10. The spinal fusion device of claim 1, wherein the actuator protruding members slidably move in the sloped slots in a first direction when the actuator is moved and the distance between the upper and lower sections decrease, and when the actuator protruding members slidably move in the sloped slots in a second direction when the actuator is moved the distance between the upper and lower sections increase.

11. The spinal fusion device of claim 1, wherein the housing is dimensioned to receive bone growth material.

12. The spinal fusion device of claim 1, wherein each said bone screw includes a locking bar to prevent removal of said bone screw upon installation.

13. The spinal fusion device of claim 12 wherein said locking bar extends across a head of each bone screw for engagement of a side surface in each said offset aperture.

14. The spinal fusion device of claim 13, wherein each said offset aperture includes a space for receipt of said locking bar, said space formed between two alignment walls.

15. The spinal fusion device of claim 14, wherein each said alignment wall provides directional placement of each said bone screw.

16. The spinal fusion device of claim 12 wherein said lock bar is positioned between each said offset aperture, said lock bar rotating between an unlocked position allowing insertion of a bone screw to a locked position preventing removal of an installed bone screw.

* * * * *